(12) United States Patent
Heinelt et al.

(10) Patent No.: US 6,825,231 B2
(45) Date of Patent: *Nov. 30, 2004

(54) SUBSTITUTED NORBORNYLAMINO DERIVATIVES, PROCESSES FOR THEIR PREPARATION, THEIR USE AS MEDICAMENTS OR DIAGNOSTICS, AND A MEDICAMENT COMPRISING THEM

(75) Inventors: Uwe Heinelt, Wiesbaden (DE); Hans-Jochen Lang, Hofheim (DE); Heinz-Werner Kleemann, Bischofsheim (DE); Jan-Robert Schwark, Kelkheim (DE); Klaus Wirth, Kriftel (DE); Hans-Willi Jansen, Niedernhausen (DE)

(73) Assignee: Aventis Pharma Deutschland GmbH, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 81 days.

(21) Appl. No.: 09/734,008

(22) Filed: Dec. 12, 2000

(65) Prior Publication Data
US 2001/0023257 A1 Sep. 20, 2001

(30) Foreign Application Priority Data
Dec. 14, 1999 (DE) .......................... 199 60 204

(51) Int. Cl.[7] .................... A61K 31/335; C07D 317/46; C07C 215/44; C07C 317/08

(52) U.S. Cl. ................. 514/467; 514/603; 514/637; 549/451; 564/373; 564/364

(58) Field of Search .................. 562/442; 558/422; 560/37; 564/164, 373, 384, 387, 391, 389, 374, 378; 514/467, 524, 555, 603, 637; 549/451

(56) References Cited

U.S. PATENT DOCUMENTS

| 4,024,274 A | 5/1977 | Druckrey et al. | |
| 6,005,010 A | 12/1999 | Schwark et al. | 514/616 |

FOREIGN PATENT DOCUMENTS

| EP | 0 825 178 A1 | 2/1998 |
| WO | WO 96/40151 | 12/1996 |

OTHER PUBLICATIONS

Schwark et al., S3226, a Novel Inhibitor of Na+/H+ Exchanger Subtype 3 in Various Cell Types, Eur. J. Physiol. (1998) 436:797–800.

Stille, J. K. et al., "The Stereospecific Additon of Carbon and Nitrogen Nucleophiles to Dicyclopentadieneplatinum and – palladium Complexes," J. Am. Chem. Soc'y, 92:5 (Mar. 11,1970), pp. 1274–1278.

(List continued on next page.)

*Primary Examiner*—Cecilia Tsang
*Assistant Examiner*—Ebenezer Sackey
(74) *Attorney, Agent, or Firm*—Finnegan, Henderson, Farabow, Garrett & Dunner, L.L.P.

(57) ABSTRACT

The application discloses substituted norbornylamino derivatives, processes for their preparation, their use as medicaments or diagnostics and a medicament comprising them Substituted norbornylamino derivatives having exo-configured nitrogen and an endo-fused five-membered ring of the formula I, or having exo-configured nitrogen and an exo-fused five-membered ring of the formula I a

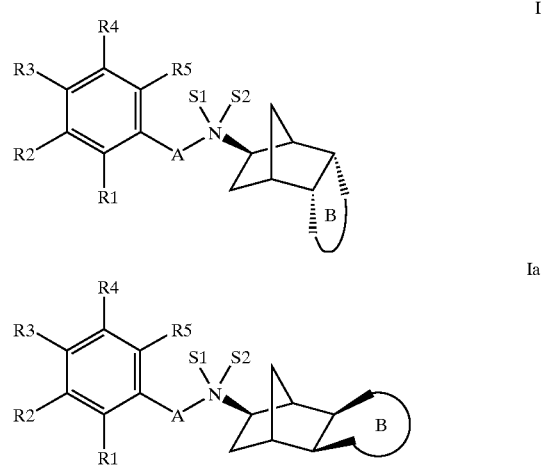

in which R1, R2, R3, R4, R5, A, B, S1, and S2 are as defined in the claims, are highly suitable for use as antihypertensive agents, for reducing or preventing ischemically induced damage, for use as medicaments for surgical interventions for the treatment of ischemias of the nervous system, of stroke and cerebral edema, of shock, of impaired respiratory drive, for the treatment of snoring, as laxatives, as agents against ectoparasites, for the prevention of the formation of biliary calculus, as antiatheroscleroticcs, as agents against late diabetic complications, carcinomatous disorders, fibrotic disorders, endothelial dysfunction, and organ hypertrophies and hyperplasias.

They are inhibitors of the cellular sodium/proton antiporter. They have an influence on serum lipoproteins and can therefore be used for the prophylaxis and regression of atherosclerotic changes.

37 Claims, No Drawings

OTHER PUBLICATIONS

S. Akhter et al., "Squalamine, a novel cationic steroid, specifically inhibits the brush–border Na+/H+ exchanger isoform NHE3," *Am. Physiological Soc'y*, 1999, pp. C136–C144.

Chung–Ming Tse et al., "Cloning and Expression of a Rabbt cDNA Encoding a Serum–activated Ethylisopropy-lamiloride–resistant Epithelial Na+/H+ Exchanger Isoforn (NHE–2)," *J. Biological Chem.*, vol. 266, No. 16, (Jun. 5, 1993), pp. 11917–11924.

John Orlowski et al. "Molecular Cloning of Putative Members of the Na/H Exchanger Gene Family," *J. Biological Chem.*, vol. 257, No. 13, (May 5, 1992), pp. 9331–9339.

Larry Fliegal et al., "Regulation and characterization of the Na+/H+exchanger," *Biochem. Cell. Biol.*, 76, pp. 735–741 (1998).

P. Atursson et al., "Correlation Between Oral Drug Absorption in Humans and Apparent Drug Permeability Coefficients in Human Intestinal Epithelial (CACO–2) Cells," *Biochemical and Biophysical Research Communications*, vol. 175, No. 3 (Mar. 29, 1991), pp. 880–885.

Claude Sardet et al., "Molecular Cloning, Primary Structure, and Expression of the Human Growth Factor—Activatable Na+/H+ Antiporter," *Cell*, vol. 56 (Jan. 27, 1989), pp. 271–280.

E. Ma et al., "Expression and Localization of Na+/H+ Exchangers in Rat Central Nervous system," *Neuroscience*, vol. 79, No. 2 (1997), pp. 591–603.

Arlette Franchi et al., "Functional expression of a human Na+/H+ antiporter gene transfected into antiporter–deficient mouse L cells," *Proc. Natl. Acad. Sci. USA*, vol. 83 (Dec. 1986), pp. 9388–9392.

F. Bondavalli et al., "Synthesis and Pharmacological Activity of Derivatives of *Exo*–trimethylenenorbornane," *Il Farmaco—Edizione Scientifica*, vol. 34, No. 11 (Nov. 1979), pp. 945–951.

SUBSTITUTED NORBORNYLAMINO DERIVATIVES, PROCESSES FOR THEIR PREPARATION, THEIR USE AS MEDICAMENTS OR DIAGNOSTICS, AND A MEDICAMENT COMPRISING THEM

DESCRIPTION OF THE INVENTION

The invention relates to substituted norbornylamino derivatives having exo-configured nitrogen and an endo-fused five-, six- or seven-membered ring of the formula I, or having exo-configured nitrogen and an exo-fused five-, six- or seven-membered ring of the formula I a

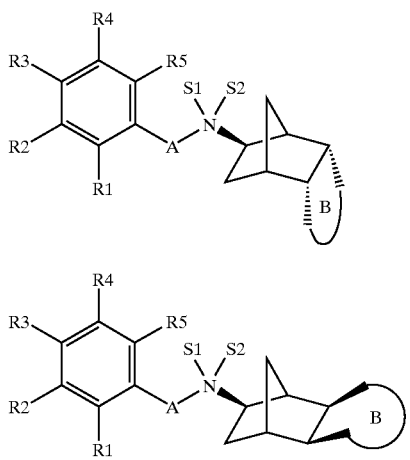

in which:

A is $(C_1-C_4)$-alkylene;

S1 is a free electron pair or $(C_1-C_4)$-alkyl;

S2 is $(C_1-C_4)$-alkyl or H;

where, if S1 and S2 are alkyl, X in the resulting grouping [—N$^+$(S1S2)-X$^-$] corresponds to a pharmacologically acceptable anion or trifluoroacetate;

B is a saturated or unsaturated five-, six- or seven-membered carbon ring which may be mono- or, independently of one another, polysubstituted by oxo, hydroxyl, $(C_1-C_4)$-alkoxy and $(C_1-C_4)$-alkyl; and R1, R2, R3, R4 and R5 are, independently of one another, H, OH, F, Cl, Br, I, CN, NO$_2$, amidino, —CO$_2$R(11), —CONR(11)R(12), —SO$_r$R(11), —SO$_s$NR(11)-R(12), $(C_1-C_4)$-alkyl, $(C_1-C_4)$-alkoxy, $(C_1-C_4)$-alkoxy-$(C_1-C_4)$-alkyl, $(C_1-C_4)$-alkoxy-$(C_1-C_4)$-alkyloxy, hydroxy-$(C_1-C_4)$-alkyl, $(C_3-C_7)$-cycloalkoxy or phenyloxy, where phenyl is unsubstituted or substituted by up to three substituents, which are independent of one another and selected from the group consisting of F, Cl, Br and methoxy;

amino, $(C_1-C_4)$-alkylamino, di-$(C_1-C_4)$-alkylamino, amino-$(C_1-C_4)$-alkyl, di-$(C_1-C_4)$-alkylamino-$(C_1-C_4)$-alkyl, $(C_1-C_4)$-alkylamino-$(C_1-C_4)$-alkyl, where some or all of the hydrogen atoms in the alkyl radicals may be substituted by fluorine;

R11 and R12 are, independently of one another, H or $(C_1-C_4)$-alkyl, where some or all of the hydrogen atoms in the alkyl radicals may be substituted by fluorine;

r is 0, 1 or 2;

s is 1 or 2; or

R1 and R2, R2 and R3, R3 and R4 or R4 and R5 in each case together are a group —O—$(CH_2)_n$—O—;

n is 1 or 2; and the radicals R1, R2, R3, R4 or R5 which remain in each case are, independently of one another, H, OH, F, Cl, Br, I, CN, NO$_2$, amidino, —CO$_2$R(11), —CONR(11)R(12), —SO$_r$R(11), —SO$_s$NR(11)-R(12), $(C_1-C_4)$-alkyl, $(C_1-C_4)$-alkoxy, $(C_1-C_4)$-alkoxy-$(C_1-C_4)$-alkyl, $(C_3-C_7)$-cycloalkoxy, hydroxy-$(C_1-C_4)$-alkyl, amino, $(C_1-C_4)$-alkylamino, di-$(C_1-C_4)$-alkylamino, amino-$(C_1-C_4)$-alkyl, di-$(C_1-C_4)$-alkylamino-$(C_1-C_4)$-alkyl, $(C_1-C_4)$-alkylamino-$(C_1-C_4)$-alkyl, where some or all of the hydrogen atoms in the alkyl radicals may be substituted by fluorine;

R11 and R12 are, independently of one another, H or $(C_1-C_4)$-alkyl, where some or all of the hydrogen atoms in the alkyl radicals may be substituted by fluorine;

r is 0, 1 or2;

s is 1 or 2;

except for benzyl(octahydro-4,7-methanoinden-5-yl) amine, and their pharmaceutically acceptable salts or trifluoroacetates.

Preference is given to compounds having exo-configured nitrogen and an endo-fused five- or six-membered ring of the formula I, or having exo-configured nitrogen and an exo-fused five- or six-membered ring of the formula I a, in which:

A is $(C_1-C_2)$-alkylene;

S1 is a free electron pair or methyl;

S2 is H;

B is a saturated or unsaturated five- or six-membered carbon ring;

R1, R2, R3, R4 and R5 are, independently of one another, H, amino, hydroxymethyl, OH, methoxy, F, Cl, Br or iodine; or R2 and R3 together are —O—CH$_2$—O—; and the remaining radicals R1, R4 and R5 are, independently of one another, H, OH, F, Cl, Br, I, CN, NO$_2$, $(C_1-C_2)$-alkoxy, amino, $(C_1-C_2)$-alkylamino or di-$(C_1-C_2)$-alkylamino, where some or all of the hydrogen atoms in the alkyl radicals may be substituted by fluorine;

except for benzyl(octahydro-4,7-methanoinden-5-yl) amine, and their pharmaceutically acceptable salts or trifluoroacetates.

Particular preference is given to compounds having exo-configured nitrogen and an endo-fused five- or six-membered ring of the formula I, or having exo-configured nitrogen and an exo-fused five- or six-membered ring of the formula I a, in which:

A is $(C_1-C_2)$-alkylene;

S1 is a free electron pair;

S2 is H;

B is a saturated or unsaturated five- or six-membered carbon ring;

R1, R3 and R5 are hydrogen;

and R2 and R4 are, independently of one another, H, methoxy, F or Cl; or

R2 and R3 together are —O—CH$_2$—O—; and

R1, R4 and R5 are hydrogen;

except for benzyl(octahydro)-4,7-methanoinden-5-yl) amine, and their pharmaceutically acceptable salts or trifluoroacetates.

Very particular preference is given to the following compounds, having exo-configured nitrogen and an endo-fused five- or six-membered ring of the formula I, or having exo-configured nitrogen and an exo-fused five-membered ring of the formula I a:

exo/endo-(3-chlorobenzyl)(octahydro-4,7-methanoinden-5-yl)amine, exo/endo-(3-fluorobenzyl)(octahydro-4,7-methanoinden-5-yl)amine, exo/endo-benzo[1,3]dioxol-5-ylmethyl(octahydro-4,7-methanoinden-5-yl)-amine, exo/endo-(rac)-(3-methoxybenzyl)(octahydro-4,7-methanoinden-5-yl)-amine, exo/endo-(+)-(3-methoxybenzyl)(octahydro-4,7-methanoinden-5-yl)amine, exo/endo-(−)-(3-methoxybenzyl)(octahydro-4,7-methanoinden-5-yl)amine, exo/endo-[1-(3-methoxyphenyl)ethyl](octahydro-4,7-methanoinden-5-yl)-amine, exo/endo-(3-fluorobenzyl)(3a,4,5,6,7,7a-hexahydro-1H-4,7-methanoinden-5-yl)amine, exo/endo-(3-fluorobenzyl)(3a,4,5,6,7,7a-hexahydro-3H-4,7-methanoinden-5-yl)amine, exo/endo-(3a,4,5,6,7,7a-hexahydro-1H-4,7-methanoinden-5-yl)(3-methoxybenzyl)amine, exo/endo-(3a,4,5,6,7,7a-hexahydro-3H-4,7-methanoinden-5-yl)(3-methoxybenzyl)amine, exo/endo-(decahydro-1,4-methanonaphthalen-2-yl)(3-methoxybenzyl)-amine, exo/endo-(3,5-difluorobenzyl)(octahydro-4,7-methanoinden-5-yl)amine, exo/exo-(3-fluorobenzyl)(octahydro-4,7-methanoinden-5-yl)amine, and exo/exo-(3-methoxybenzyl)(octahydro-4,7-methanoinden-5-yl)amine, and their pharmaceutically acceptable salts or trifluoroacetates.

Most particular preference is given to the following compounds, having exo-configured nitrogen and an endo-fused five- or six-membered ring of the formula I:

exo/endo-(3-chlorobenzyl)(octahydro-4,7-methanoinden-5-yl)amine, exo/endo-(3-fluorobenzyl)(octahydro-4,7-methanoinden-5-yl)amine, exo/endo-(3-fluorobenzyl)(3a,4,5,6,7,7a-hexahydro-1H-4,7-methanoinden-5-yl)amine, exo/endo-(3-fluorobenzyl)(3a,4,5,6,7,7a-hexahydro-3H-4,7-methanoinden-5-yl)amine, exo/endo-benzo[1,3]dioxol-5-ylmethyl(octahydro-4,7-methanoinden-5-yl)-amine, exo/endo-(rac)-(3-methoxybenzyl)(octahydro-4,7-methanoinden-5-yl)amine, exo/endo-(+)-(3-methoxybenzyl)(octahydro-4,7-methanoinden-5-yl)amine, exo/endo-(decahydro-1,4-methanonaphthalen-2-yl)(3-methoxybenzyl)-amine, exo/endo-(−)-(3-methoxybenzyl)(octahydro-4,7-methanoinden-5-yl)amine, and exo/endo-(3,5-difluorobenzyl)(octahydro-4,7-methanoinden-5-yl)amine, and their pharmaceutically acceptable salts or trifluoroacetates.

Suitable acid addition salts are the salts of all pharmacologically acceptable acids, for example halides, in particular hydrochlorides, lactates, sulfates, citrates, tartrates, acetates, phosphates, methylsulfonates, p-toluene-sulfonates, adipates, fumarates, gluconates, glutamates, glycerol phosphates, maleates, and pamoates. This group also corresponds to the pharmacologically acceptable anions. However, trifluoroacetates are also suitable.

If the compound of the formula I or Ia contains one or more centers of asymmetry, these can be either S- or R-configured. The compounds can be present as optical isomers, diastereomers, racemates, or mixtures thereof. However, the amino substituent has to be in the exo position and the ring has to be endo- and exo-fused, respectively.

The alkyl or alkylene radicals mentioned can be straight-chain or branched.

The invention furthermore relates to a process for preparing the compounds of the formula I or I a, which comprises a) reacting a compound of the formula II or II a

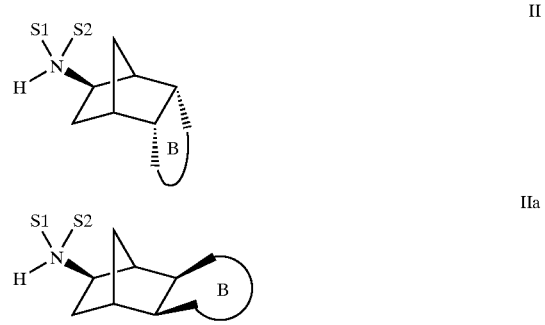

with a compound of the formula III

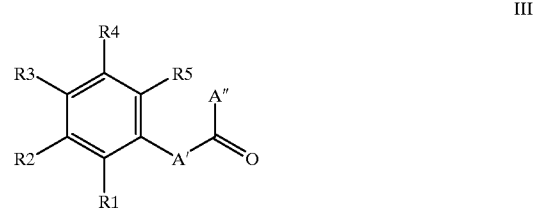

in which S1, S2, B, R1, R2, R3, R4 and R5 are as defined above, while independently of one another A' is a bond or $(C_1–C_3)$-alkylene and A" is H or $(C_1–C_3)$-alkyl and A' and A" together with the carbon atom of the carbonyl group represent the same number of carbon atoms as A, in the presence of suitable reducing agents and optionally also Lewis acids directly to give compounds of the formula I or I a; or b) isolating the intermediate of the formula IV or IV a

IV

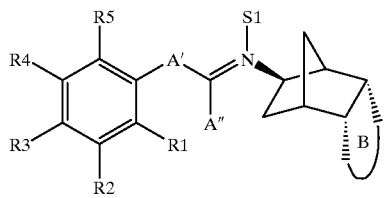

IVa

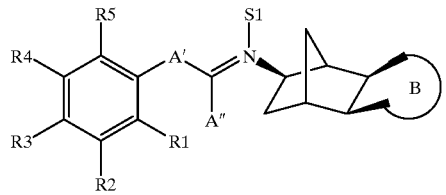

formed from compounds of the formulae II or II a and III, in which, if S1 is $(C_1–C_4)$-alkyl, an onium nitrogen is formed which is associated with a counterion, such as, for example, chloride or tosylate, and then converting the intermediate with suitable reducing agents into the compounds of the formula I or Ia; or c) reacting a compound of the formula II or II a with an alkylating agent of the formula V

V

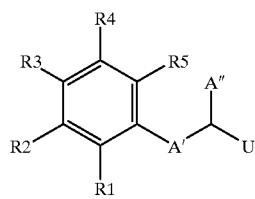

in which U is a nucleophilically substitutable group—such as chlorine, bromine and iodine and also mesylate, tosylate or triflate or another good leaving group—and the other radicals are as defined above, but where the carbon atom to which U is attached corresponds to the carbon atom of the carbonyl group, preferably in the presence of non-nucleophilic bases, such as diisopropyl-ethylamine; or d) reducing carboxamides of the formula VI or VI a

VI

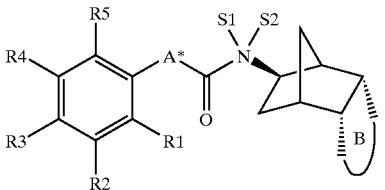

VIa

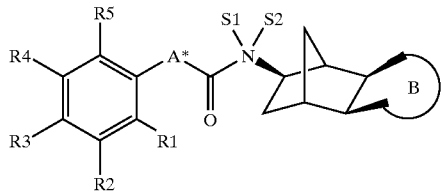

in which A* is a bond or $(C_1–C_3)$-alkylene and the other radicals are as defined above
to give the corresponding amines; or e) mono- or dialkylating compounds of the formula I or Ia in which S1 is a free electron pair and S2 is hydrogen, with alkylating agents of the formula VII

S*—U      VII in which S* is $(C_1–C_4)$-alkyl and U is as defined above, thus obtaining tertiary amines or quaternary ammonium salts; or f) reacting a dicyclopentadienylplatinum complex of the formula VIII

VIII

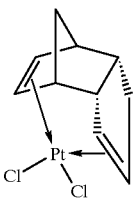

with amines of the type of the formula IX

IX

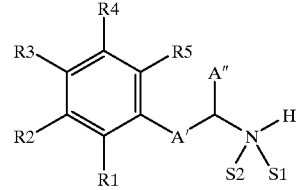

in which S1, S2, R1, R2, R3, R4 and R5 are as defined above, while independently of one another A' is a bond or $(C_1–C_3)$-alkylene and A" is H or $(C_1–C_3)$-alkyl and A' and A" together with the carbon atom to which the nitrogen atom is attached represent the same number of carbon atoms as A, and then reducing the intermediate formed to give compounds of the formula I (J. K. Stille, D. B. Fox JACS 1970 (92), 1274);

optionally followed by conversion into the pharmaceutically acceptable salt or trifluoroacetate.

U.S. Pat. No. 4,024,274 (Hoe 74/F018) describes norbornylamines having a similar type of structure, but an unknown steric structure, which have good diuretic and saluretic activity.

During screening of the large number of examples given in that patent, it was surprisingly found that some compounds of this type of structure are potent inhibitors of the sodium/proton exchanger, subtype 3 (NHE3). The most potent compound was then examined for its salidiuretic activity and, surprisingly, it was not possible to demonstrate any salidiuretic activity, so that a connection between NHE3 activity and salidiuresis could not be shown.

Since the steric structure of the tricycle was unknown, there was a choice between four possible pairs of enantiomers, i.e., a total of eight sterically different structures. For these pairs of enantiomers, it was found that only two pairs have a potent NHE3-inhibiting activity, whereas the other two pairs of enantiomers have hardly any NHE3-blocking properties. Elucidation of the most active structure by X-ray analysis showed that the most highly NHE3-active pair of enantiomers are compounds having a defined exo-configuration for the nitrogen and a defined endo-fused five-membered ring. The pair of enantiomers which is slightly less active has the defined exo-configuration for the nitrogen and a defined exo-fused five-membered ring. The two remaining pairs of enantiomers having defined endo/exo and endo/endo configuration, respectively, show hardly any NHE3-inhibiting activity.

Furthermore, it was surprising that the defined separated enantiomers of one of the exemplary compounds having the defined exo-configuration for the nitrogen and the defined endo-fused five-membered ring were both of similar activity at the NHE3. Owing to their enantiomeric steric arrangement, a considerable difference in activity was expected here.

With respect to the known inhibitors of the sodium/proton exchanger, subtype 3, according to EP-A 825 178 (HOE 96/F226), which represent relatively polar structures and correspond to the acylguanidine type (J.-R. Schwark et al. Eur. J. Physiol (1998) 436:797), the compounds according to the invention are surprisingly lipophilic substances which are not of the acylguanidine type and which represent entirely novel structures for the inhibition of NHE3. According to our searches, they are, after the acylguanidines just mentioned and the delayed acting squalamine (M. Donowitz et al. Am. J. Physiol. 276 (Cell Physiol. 45): C136–C144; activity seen after one hour) only the third class of substances of NHE3 inhibitors which has hitherto been disclosed. Compared with the abovementioned known NHE3 inhibitors, they are better able to cross membranes and show no delay of their inhibitory effect.

The NHE3 is found in the body of various species, preferably in the gall bladder, the intestine, and the kidney (Larry Fliegel et al., Biochem. Cell. Biol. 76: 735–741, 1998), but it was also detected in the brain (E. Ma et al. Neuroscience 79: 591–603).

The compounds of the formula I or I a according to the invention are suitable for use as antihypertensives for the treatment of primary and secondary hypertension.

Moreover, the compounds on their own or in combination with NHE inhibitors of other subtype specificity can protect organs which are acutely or chronically undersupplied with oxygen by reducing or preventing ischemically induced damage. They are thus suitable as medicaments, for example for surgical interventions (e.g., in kidney and liver organ transplantation, where the compounds can be used for the protection of the organs in the donor before and during removal, for the protection of removed organs, for example during treatment with or storage thereof in physiological bath fluids, and in the transfer to the recipient's body) or acute or chronic kidney failure. Particularly advantageously, they can be employed for preventing ischemically induced damage to the intestine.

Corresponding to their protective action against ischemically induced damage, the compounds are potentially also suitable as medicaments for the treatment of ischemias of the nervous system, in particular of the CNS, where they are suitable, for example, for the treatment of stroke or of cerebral edema. Moreover, the compounds of the formula I or Ia according to the invention are likewise suitable for the treatment of forms of shock, such as, for example, of allergic, cardiogenic, hypovolemic, and of bacterial shock.

The compounds furthermore induce an improvement in the respiratory drive and are therefore used for the treatment of respiratory conditions in the following clinical conditions and illnesses: impaired central respiratory drive (for example central sleep apneas, sudden infant death, postoperative hypoxia), muscle-related respiratory disorders, respiratory disorders after long-term respiration, respiratory disorders during adaptation in high mountain regions, obstructive and mixed forms of sleep apneas, acute and chronic lung diseases with hypoxia and hypercapnia.

Additionally, the compounds increase the muscle tone of the upper respiratory tract, thus suppressing snoring.

A combination of an NHE inhibitor with a carboanhydrase inhibitor (for example acetazolamide), the latter producing a metabolic acidosis and thereby even increasing respiratory activity, proves to be a favorable combination with increased action and decreased use of active compound.

It has been found that the compounds according to the invention have a mild laxative effect, and they can therefore advantageously be used as laxatives or for imminent bowel obstruction, where the prevention of ischemic damage associated with obstruction in the intestinal area is particularly advantageous.

It is furthermore possible to prevent formation of biliary calculus.

The compounds of the formula I or Ia according to the invention may additionally have an inhibiting effect on the proliferation of cells, for example fibroblast cell proliferation and the proliferation of vascular smooth muscle cells. The compounds of the formula I or Ia are therefore suitable as valuable therapeutics for illnesses in which cell proliferation is a primary or secondary cause, and can therefore be used as antiatherosclerotics and as agents against late diabetic complications, carcinomatous disorders, fibrotic disorders, such as pulmonary fibrosis, hepatic fibrosis, or renal fibrosis, endothelial dysfunction, and organ hypertrophies and hyperplasias, in particular prostate hyperplasia or prostate hypertrophy.

The compounds according to the invention are effective inhibitors of the cellular sodium/proton antiporter, which is raised in numerous disorders (essential hypertension, atherosclerosis, diabetes, etc.) even in those cells which are easily accessible to measurements, such as, for example, in erythrocytes, platelets, or leucocytes. The compounds according to the invention are therefore suitable as outstanding and simple scientific tools, for example in their use as diagnostics for the determination and differentiation of certain forms of hypertension, but also of atherosclerosis, of diabetes, proliferative disorders, etc. Moreover, the compounds of the formula I or I a are suitable for preventive therapy for preventing the genesis of high blood pressure, for example, of essential hypertension.

It has additionally been found that NHE inhibitors have a favorable influence on the serum lipoproteins. It is generally recognized that the formation of arteriosclerotic vascular changes, in particular of coronary heart disease, excessively high blood lipid values, so-called hyperlipoproteinemias, are a significant risk factor. The lowering of raised serum lipoproteins is therefore of extreme importance for the prophylaxis and regression of atherosclerotic changes. The compounds according to the invention can therefore be used for the prophylaxis and for the regression of atherosclerotic changes, in that they exclude a causal risk factor. With this protection of the vessels against the endothelial dysfunction syndrome, the compounds of the formula I or I a are valuable medicaments for the prevention and for the treatment of coronary vasospasms, atherogenesis and atherosclerosis, left-ventricular hypertrophy and dilated cardiomyopathy, and thrombotic disorders.

The compounds mentioned are therefore used advantageously for the production of a medicament for the prevention and treatment of sleep apneas and muscle-related respiratory disorders; for the production of a medicament for the prevention and treatment of snoring; for the production of a medicament for lowering blood pressure; for the production of a medicament having a laxative effect for the prevention and treatment of intestinal obstructions; for the production of a medicament for the prevention and treatment of disorders caused by ischemia and reperfusion of central and peripheral organs and limbs, such as acute kidney failure, stroke, endogenous states of shock, intestinal disorders, etc.; for the production of a medicament for the treatment of hypercholesterolemia; for the production of a medicament for the prevention of atherogenesis and atherosclerosis; for the production of a medicament for the prevention and treatment of diseases caused by elevated cholesterol levels; for the production of a medicament for the prevention and treatment of diseases caused by endothelial dysfunction; for the production of a medicament for the treatment of infestation by ectoparasites; and for the production of a medicament for the treatment of the illnesses mentioned in combinations with hypotensive substances, preferably with angiotensin-converting enzyme (ACE) inhibitors and angiotensin receptor antagonists. A combination of an NHE inhibitor of the formula I or I a with a blood lipid level-lowering active compound, preferably with an HMG-CoA-reductase inhibitor (for example lovastatin or pravastatin), where the latter produces a hypolipidemic action and thereby increases the hypolipidemic properties of the NHE inhibitor of the formula I or I a, proves to be a favorable combination with increased action and decreased use of active compound.

The invention includes the administration of sodium/proton exchange inhibitors of the formula I or I a as novel medicaments for lowering increased blood lipid levels, and also the combination of sodium/proton exchange inhibitors with hypotensive and/or hypolipidemic medicaments.

Medicaments that contain a compound I or I a can be administered orally, parenterally, intravenously, rectally, or by inhalation, the preferred administration being dependent on the particular clinical picture of the disorder. The compounds I or I a can be used on their own or together with pharmaceutical auxiliaries, both in veterinary and in human medicine.

The person skilled in the art is familiar on the basis of his expert knowledge with auxiliaries, that are suitable for the desired pharmaceutical formulation. Besides solvents, gel-forming agents, suppository bases, tablet auxiliaries and other active compound excipients, it is possible to use, for example, antioxidants, dispersants, emulsifiers, antifoams, flavor corrigents, preservatives, solubilizers, or colorants.

For an oral administration form, the active compounds are mixed with the additives suitable for this purpose, such as excipients, stabilizers, or inert diluents, and are brought by means of the customary methods into the suitable administration forms, such as tablets, coated tablets, hard gelatin capsules, or aqueous, alcohol, or oily solutions. Inert excipients that can be used are, for example, gum arabic, magnesia, magnesium carbonate, potassium phosphate, lactose, glucose, or starch, in particular corn starch. In this case preparation can take place either as dry or as moist granules. Suitable oily excipients or solvents are, for example, vegetable or animal oils, such as sunflower oil or cod-liver oil.

For subcutaneous or intravenous administration, the active compounds are brought into solution, suspension, or emulsion, if desired, using the substances customary for this purpose, such as solubilizers, emulsifiers, or other auxiliaries. Possible solvents are, for example: water; physiological saline solution or alcohols, for example ethanol, propanol, glycerol; or sugar solutions, such as glucose or mannitol solutions; or alternatively a mixture of the various solvents mentioned.

Suitable pharmaceutical formulations for administration in the form of aerosols or sprays are, for example, solutions, suspensions, or emulsions of the active compound of the formula I or I a in a pharmaceutically acceptable solvent, such as, in particular, ethanol or water, or a mixture of such solvents.

If required, the formulation can also contain other pharmaceutical auxiliaries, such as surfactants, emulsifiers, and stabilizers, and also a propellant. Such a preparation contains the active compound customarily in a concentration of from approximately 0.1 to 10, in particular from approximately 0.3 to 3, % by weight.

The dosage of the active compound of the formula I or I a to be administered and the frequency of administration depend on the potency and duration of action of the compounds used, additionally also on the nature and severity of the illness to be treated and on the sex, age, weight, and individual responsiveness of the mammal to be treated.

On average, the daily dose of a compound of the formula I or I a in the case of a patient of approximately 75 kg in weight is at least 0.001 mg/kg, preferably 1–10 mg/kg, to at most 100 mg/kg, of body weight. In acute episodes of the illnesses, even higher and especially more frequent doses may also be necessary, for example up to four individual doses per day. In particular on i.v. administration, for example in the case of an infarct patient in the intensive care unit, up to 200 mg per day may be necessary.

Experimental Section:

| Abbreviations used: | |
|---|---|
| $CH_2Cl_2$ | dichloromethane |
| CI | chemical ionization |
| DIP | diisopropyl ether |
| EA | ethyl acetate |
| ES | electrospray |
| HOAc | acetic acid |
| $H_2O$ | water |
| $H_2O_2$ | hydrogen peroxide |
| bp | boiling point |
| MeOH | methanol |
| $MgSO_4$ | magnesium sulfate |
| mp | melting point |
| MS | mass spectrum |
| MTB | methyl tert-butyl ether |
| $NaBH_4$ | sodium borohydride |
| $NaHCO_3$ | sodium bicarbonate |
| NaOH | sodium hydroxide |
| RT | room temperature |
| THF | tetrahydrofuran |
| TFA | trifluoroacetic acid |
| HCl | hydrochloric acid |

Description of the Synthesis of Some Amines:
Amine 1)
Synthesis of the exo/endo-configured octahydro-4,7-methanoinden-5-ylamine:

a1) bis-(6-chloro-3a,4,5,6,7,7a-hexahydro-1H-4,7-methanoinden-5-yl)-diazene N,N'-dioxide and isomers

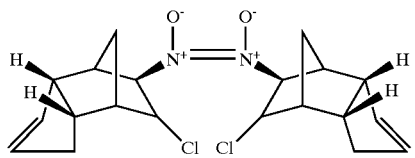

167 g of isoamyl nitrite were added to a mixture of 167 g of dicyclopenta-diene, 160 ml of glacial acetic acid and 160 ml of ethanol, and at −10° C., 420 ml of a 15% strength solution of hydrogen chloride in ethanol were then added dropwise with stirring. The mixture was stirred at room temperature for a further 3 hours. 500 ml of diisopropyl ether were added, the mixture was stirred for a further 10 minutes, and the crystals were then filtered off. Virtually colorless crystals, mp. 177–178° C.

b1) octahydro-4,7-methanoinden-5-ylamine

A suspension of 10 g of bis-(6-chloro-3a,4,5,6,7,7a-hexahydro-1H-4,7-methanoinden-5-yl)diazene N,N'-dioxide, 60 ml of methanol and Raney nickel was hydrogenated at 100° C. and under an $H_2$ pressure of 100 atm for 10 hours. The catalyst was filtered off, the solvent was evaporated under reduced pressure using a rotary evaporator, the semicrystalline residue was mixed with water, and the mixture was made strongly alkaline by addition of 10 N NaOH. The mixture was extracted 3 to 4 times with methyl tert-butyl ether and the organic phases were dried over sodium sulfate, and the solvent was then distilled off and the oil was rectified under reduced pressure. $Bp_{5mm}$ 86–91° C.
or
a2) 3a,4,5,6,7,7a-hexahydro-1H-4,7-methanoinden-5-ylamine and 3a,4,5,6,7,7a-hexahydro-3H-4,7-methanoinden-5-ylamine

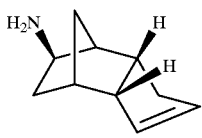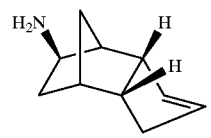

20 g of exo-5-isothiocyanato-5,6-dihydroendodicyclopentadiene (Maybridge International) were dissolved in 60 ml of formic acid, and the solution was boiled under reflux for 27 hours. The volatile components were removed under reduced pressure, 50 ml of a 20% strength aqueous NaOH solution were added, and the mixture was extracted three times with, in each case, 100 ml of $CH_2Cl_2$. The extracts were dried over $MgSO_4$ and the solvent was removed under reduced pressure. This gave 13.4 g of a pale yellow oil.
$R_f(CH_2Cl_2/MeOH/HOAc/H_2O$ 32:8:1:1)=0.57; MS (ES+): 150 $(M+H)^+$ b2) tert-butyl (3a,4,5,6,7,7a-hexahydro-1H-4,7-methanoinden-5-yl)-carbamate and tert-butyl (3a,4,5,6,7,7a-hexahydro-3H-4,7-methanoinden-5-yl)carbamate 12.8 g of a mixture of 3a,4,5,6,7,7a-hexahydro-1H-4,7-methanoinden-5-ylamine and 3a,4,5,6,7,7a-hexahydro-3H-4,7-methanoinden-5-ylamine were dissolved in 200 ml of THF and, at RT, admixed with a solution of 18.7 g of di-tert-butyl dicarbonate in 200 ml of THF. 12 ml of triethylamine were then added dropwise, and the mixture was stirred at RT for 2 hours. The volatile components were removed under reduced pressure and the residue was chromatographed over silica gel using DIP. This gave 15 g of a colorless oil which was crystallized from n-heptane; mp 94° C.

$R_f$(DIP)=0.68 MS (Cl+): 250 $(M+H)^+$ c2) tert-butyl (octahydro-4,7-methanoinden-5-yl)carbamate
500 mg of a mixture of tert-butyl (3a,4,5,6,7,7a-hexahydro-1H-4,7-methanoinden-5-yl)carbamate and tert-butyl (3a,4,5,6,7,7a-hexahydro-3H-4,7-methanoinden-5-yl) carbamate were dissolved in 20 ml of methanol and 2 ml of acetic acid and hydrogenated under an atmosphere of hydrogen (1 bar) for 6 hours, with the aid of 200 mg of Pd/C 10% (50% water). The catalyst was filtered off and the volatile components were removed under reduced pressure. This gave 470 mg of a resin-like amorphous solid.

$R_f$(DIP)=0.70 MS (Cl+): 252 $(M+H)^+$ d2) octahydro-4,7-methanoinden-5-ylamine trifluoroacetate
460 mg of tert-butyl (octahydro-4,7-methanoinden-5-yl)carbamate were dissolved in 5 ml of trifluoroacetic acid, and the mixture was stirred at RT for 24 hours. The volatile components were then removed under reduced pressure, giving 390 mg of a pale yellow foam.

$R_f(EA/HEP/MeOH/CH_2Cl_2$/saturated aqueous $NH_3$ solution 10:5:5:5:1)=0.30

MS (Cl+): 152 $(M+H)^+$ or a3) octahydro-4,7-methanoinden-5-ylamine
3.3 g of a mixture of 3a,4,5,6,7,7a-hexahydro-1H-4,7-methanoinden-5-ylamine and 3a,4,5,6,7,7a-hexahydro-3H-4,7-methanoinden-5-ylamine (example Amine 1, a2) were dissolved in 30 ml of methanol and reduced under an atmosphere of hydrogen in the presence of 0.5 g Pd/C (10%). After 4 hours the catalyst was filtered off and washed with methanol. The filtrate was concentrated in vaccuo to give 3 g of the desired product as an oil.

MS (ES+): 152 $(M+H)^+$

Amine 2)
Synthesis of the endo/exo-configured octahydro-4,7-methanoinden-5-yl-amine:

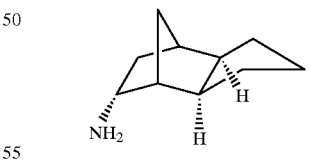

A solution of 15 g of tricyclo[5,2,1,0$^{2,6}$]decan-8-one in 60 ml of methanol, which had been saturated beforehand at 10° C. with $NH_3$, was, after addition of Raney nickel, hydrogenated in an autoclave at 90° C. and a hydrogen pressure of 100 bar for 10 hours. The catalyst was filtered off and the solvent was distilled off under reduced pressure, and the mixture was then made strongly alkaline using 10 N NaOH and extracted 2–3 times with ethyl acetate or with diisopropyl ether. The combined organic phases were dried and subjected to fractional distillation under reduced pressure. $Bp_{6-7mm}$ 86–88° C.

Amine 3)
Synthesis of the endo/endo-configured octahydro-4,7-methanoinden-5-yl-amine:

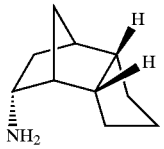

a) 1,3a,4,6,7,7a-hexahydro-4,7-methanoinden-5-one oxime 10 g of bis-(6-chloro-3a,4,5,6,7,7a-hexahydro-1H-4,7-methanoinden-5-yl)-diazene N,N'-dioxide from amine 1, a1) were suspended in 75 ml of isoamyl alcohol, and the suspension was slowly heated to reflux with stirring. Once everything had been dissolved, the mixture was cooled to room temperature using an ice bath, and 25 ml of dry ethanol, 12.5 ml of glacial acetic acid, and 6 g of zinc dust were added. The mixture was kept at reflux for 1 hour and then cooled, the zinc was filtered off, and the ethanol was evaporated under reduced pressure. The residue was stirred into 300 ml of ether and allowed to stand overnight. The ether was then decanted off from the precipitate and washed three times with sodium carbonate solution and twice with water. The organic phase was dried over magnesium sulfate and filtered, and the filtrate was then concentrated. Subsequent distillation under reduced pressure gave 3.3 g of an oil which was directly reacted further.

b) octahydro-4,7-methanoinden-5-ylamine 2.2 g of 1,3a,4,6,7,7a-hexahydro-4,7-methanoinden-5-one oxime were dissolved in 50 ml of methanol, and about 10% Raney nickel, dissolved in 50% water, was added. The mixture was hydrogenated at 100 bar and 100° C. for 20 hours, the catalyst was then filtered off, and the solvent was evaporated under reduced pressure. The residue was taken up in ether and 6 N aqueous sodium hydroxide solution, the phases were separated, the aqueous phase was extracted three times with ether, the combined organic phases were dried with magnesium sulfate and filtered, and the filtrate was concentrated. This gave 1.8 g of a colorless oil which was purified by kugelrohr distillation. This gave 0.96 g of the desired amine as an oil.

MS (Cl+): 152.2 (M+H)$^+$

Amine 4)
Synthesis of the exo/exo-configured octahydro-4,7-methanoinden-5-yl-amine:

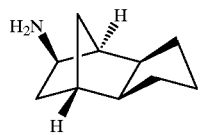

a) octahydro-4,7-methanoinden-5-ol 25 g of tricyclo[5.2.1.0 (2,6)]decan-8-one (Aldrich) were dissolved in 100 ml of methanol and, at room temperature and with slight cooling and stirring, admixed a little at a time with 6.3 g of solid sodium borohydride over a period of 2 h. The mixture was then stirred for another 2 h and allowed to stand overnight. With cooling, about 40 ml of 2 N HCl were then added dropwise, followed by 20 ml of water. The mixture was concentrated, the residue was admixed with ethyl acetate, and the ethyl acetate phase was washed once with water and once with sodium bicarbonate solution. The ethyl acetate phase was dried using magnesium sulfate and then filtered and concentrated. This gave 26 g of an oil which was purified by distillation under reduced pressure. This gave 20.7 g of an oily liquid (bp$_{0.5}$ 76° C.).

b) 2-(octahydro-4,7-methanoinden-5-yl)isoindole-1,3-dione

With stirring, 1.7 g of diethyl azodicarboxylate, diluted with 5 ml of THF, were added to a solution of 1.66 g of octahydro-4,7-methanoinden-5-ol, 1.47 g of phthalimide, and 2.62 g of triphenylphosphine in 15 ml of THF. The reaction mixture was allowed to stand overnight and then concentrated, the residue was stirred with ether, the precipitate was filtered off with suction, and the filtrate was concentrated. The residue was purified over silica gel using toluene. This gave 1.36 g of a yellow oil.

MS (Cl+): 282.2 (M+H)$^+$ c) exo/exo-octahydro-4,7-methanoinden-5-ylamine 0.4 g of hydrazine hydrate were added dropwise to a solution of 1.12 g of 2-(octahydro-4,7-methanoinden-5-yl) isoindole-1,3-dione and 15 ml of ethanol, and the mixture was stirred at 65° C. for 2 h. The pH was then adjusted to pH 1–2 using conc. HCl and admixed with 10 ml of ethanol, the precipitate was filtered off, and the filtrate was concentrated. The residue was purified by preparative HPLC over RP-18 using acetonitrile/water (0.05% trifluoroacetic acid). Freeze-drying gave 567 mg of product as the trifluoroacetate. Treatment with aqueous sodium hydroxide solution and ethyl acetate gave 322 mg of the free amine.

MS (Cl+): 152.0 (M+H)$^+$

EXAMPLES

Unless indicated otherwise, the examples given here are racemates.

Example 1

(exo/endo)-(3-chlorobenzyl)(octahydro-4,7-methanoinden-5-yl)-amine hydrochloride

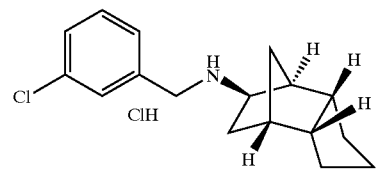

After addition of a small catalytic amount of p-toluenesulfonic acid, a solution of 0.54 g of the exo/endo-configured octahydro-4,7-methanoinden-5-ylamine (amine 1) and 0.562 g of 3-chlorobenzaldehyde in 20 ml of toluene is heated at the boil for 5 hours and then allowed to stand at room temperature overnight, after which the solvent is distilled off. The residue is dissolved in methanol, and 0.181 g of sodium borohydrate are then added in small portions with stirring to the ice-cooled yellow solution. The mixture is stirred at room temperature for several hours and then made strongly acidic using excess methanolic hydrogen chloride solution. The mixture is stirred briefly, the precipitate is filtered off, and the solvent is distilled off from the filtrate. The residue forms a colorless to slightly yellow crystalline substance, mp 241° C.

Example 2

(exo/endo)-(3-fluorobenzyl)-(3a,4,5,6,7,7a-hexahydro-1H-4,7-methanoinden-5-yl)-amine and (exo/endo)-(3-fluorobenzyl)-(3a,4,5,6,7,7a-hexahydro-3H-4,7-methanoinden-5-yl)-amine

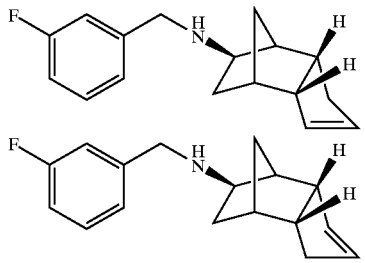

300 mg of a mixture of 3a,4,5,6,7,7a-hexahydro-1H-4,7-methanoinden-5-ylamine and 3a,4,5,6,7,7a-hexahydro-3H-4,7-methanoinden-5-ylamine (see amine 1, a2), 315 μl of 3-fluorobenzaldehyde and 10 mg of p-toluenesulfonic acid were dissolved in 5 ml of toluene (anhydrous), and the mixture was boiled under reflux for 5 hours. The volatile components were then removed under reduced pressure, the residue was taken up in 20 ml of MeOH, 152 mg of $NaBH_4$ were added, and the mixture was allowed to stand at RT for 15 hours. The reaction mixture was then diluted with 200 ml of EA and washed twice with, in each case, 50 ml of a saturated aqueous $NaHCO_3$ solution. The mixture was dried over $MgSO_4$ and the solvent was removed under reduced pressure. Preparative HPLC over RP-18 using acetonitrile/water (gradient: 5:95–95:5) gave 150 mg of a colorless oil.

$R_f$(EA)=0.40; MS (Cl+): 258 (M+H)$^+$

Example 3

(exo/endo)-(3a,4,5,6,7,7a-hexahydro-1H-4,7-methanoinden-5-yl)(3-methoxybenzyl)amine and (exo/endo)-(3a,4,5,6,7,7a-hexahydro-3H-4,7-methanoinden-5-yl)(3-methoxybenzyl)amine

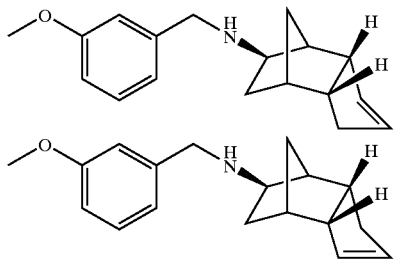

The compounds of Example 3 were synthesized analogously to Example 2.

$R_f$(EA)=0.35; MS (Cl+): 270 (M+H)$^+$

Example 4

(exo/endo)-5-(3-methoxybenzylamino)octahydro-4,7-methanoinden-2-ol

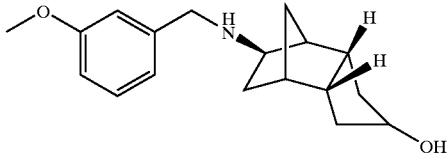

a) tert-butyl (3a,4,5,6,7,7a-hexahydro-1H-4,7-methanoinden-5-yl)-carbamate and tert-butyl (3a,4,5,6,7,7a-hexahydro-3H-4,7-methanoinden-5-yl)carbamate 12.8 g of a mixture of 3a,4,5,6,7,7a-hexahydro-1H-4,7-methanoinden-5-ylamine and 3a,4,5,6,7,7a-hexahydro-3H-4,7-methanoinden-5-ylamine were dissolved in 200 ml of THF and, at RT, admixed with a solution of 18.7 g of di-tert-butyl dicarbonate in 200 ml of THF. 12 ml of triethylamine were then added dropwise, and the mixture was stirred at RT for 2 hours. The volatile components were removed under reduced pressure. Chromatography over silica gel using DIP gave 15 g of a colorless oil. Crystallization from n-heptane gave 4.9 g of colorless crystals, mp 94° C.

$R_f$(DIP)=0.68; MS (ES+): 250 (M+H)$^+$ b) tert-butyl (2-hydroxyoctahydro-4,7-methanoinden-5-yl)carbamate 4.87 g of a mixture of tert-butyl (3a,4,5,6,7,7a-hexahydro-1H-4,7-methanoinden-5-yl)carbamate and tert-butyl (3a,4,5,6,7,7a-hexahydro-3H-4,7-methanoinden-5-yl)carbamate were dissolved in 30 ml of toluene (anhydrous) and, at RT, 20 ml of a 2 M solution of borane/dimethyl sulfide complex in toluene were added using a syringe. The mixture was stirred at RT for 24 hours, a further 10 ml of a 2 M solution of borane/dimethyl sulfide complex in toluene were added using a syringe, and the mixture was stirred at RT for another 6 hours. The volatile components were then removed under reduced pressure, 200 ml of $CH_2Cl_2$ and 33 ml of a 3 N aqueous NaOH solution were added, and the mixture was slowly admixed with 7 ml of a 30% strength aqueous $H_2O_2$ solution. The mixture was stirred at RT for 10 minutes, and a further 100 ml of a 3 N aqueous NaOH solution and 20 ml of a 30% strength aqueous $H_2O_2$ solution were added. The reaction mixture was stirred at RT for another 10 minutes and then extracted three times with, in each case, 200 ml of $CH_2Cl_2$. The extracts were dried over $MgSO_4$ and the solvent was removed under reduced pressure. Chromatography over silica gel using MTB gave 2.9 g of an amorphous solid which was still contaminated by regioisomers.

$R_f$(MTB)=0.47; MS (Cl+): 268 (M+H)$^+$ c) 5-aminooctahydro-4,7-methanoinden-2-ol trifluoroacetate 300 mg of tert-butyl (2-hydroxyoctahydro-4,7-methanoinden-5-yl)carbamate were dissolved in 3 ml of trifluoroacetic acid, and the solution was stirred at RT for 30 minutes. The volatile components were then removed under reduced pressure. This gave 340 mg of a resin-like solid which was used further as such.

$R_f$(EA/HEP/MeOH/$CH_2Cl_2$/saturated aqueous $NH_3$ solution 10:5:5:5:1)=0.28; MS (ES+): 168 (M+H)$^+$ d) 5-(3-methoxybenzylamino)octahydro-4,7-methanoinden-2-ol 309 mg of 5-aminooctahydro-4,7-methanoinden-2-ol trifluoroacetate and 225 mg of 3-methoxybenzaldehyde were dissolved in 10 ml of toluene (anhydrous), and the mixture was boiled under reflux for 5 hours. The volatile components were then removed under reduced pressure. The residue was taken up in 10 ml of MeOH, admixed with 208 mg of NaBH$_4$, and stirred at RT for 16 h. The mixture was then diluted with 100 ml of EA and washed twice with, in each case, 30 ml of a 10% strength aqueous NaHCO$_3$ solution. The organic phase was dried over MgSO$_4$ and the solvent was removed under reduced pressure. Chromatography over silica gel using EA/MeOH 2:1 gave 100 mg of an amorphous solid.

R$_f$(EA/MeOH 2:1)=0.20; MS (ES+): 288 (M+H)$^+$

Example 5 rac-(exo/endo)-(3-methoxybenzyl)(octahydro-4,7-methanoinden-5-yl)amine hydrochloride

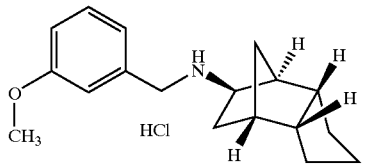

A mixture of 1.08 g of 3-methoxybenzaldehyde, 1.1 g of (exo/endo)-octahydro-4,7-methanoinden-5-ylamine (amine 1), a catalytic amount of p-toluenesulfonic acid, and 20 ml of anhydrous toluene was boiled under reflux for 3 hours, the toluene was distilled off under reduced pressure, and the residue was dissolved in 20 ml of methanol. With cooling, 0.36 g of sodium borohydride were added in small portions to this methanolic solution, and the mixture was stirred at room temperature for 18 hours. A solution of hydrogen chloride in methanol was added, the precipitate was filtered off, and the solvent was distilled off under reduced pressure. The residue was boiled in ethanol and filtered off, and 150 ml of diethyl ether were added with stirring to the filtrate. This mixture was placed in a refrigerator for several hours, and the crystalline substance was then filtered off. Colorless crystals, mp. 190–194° C.

Example 6

(+)-(exo/endo)-(3-methoxybenzyl)(octahydro-4,7-methanoinden-5-yl) amine hydrochloride and
(−)-(exo/endo)-(3-methoxybenzyl)(octahydro-4,7-methanoinden-5-yl)amine hydrochloride

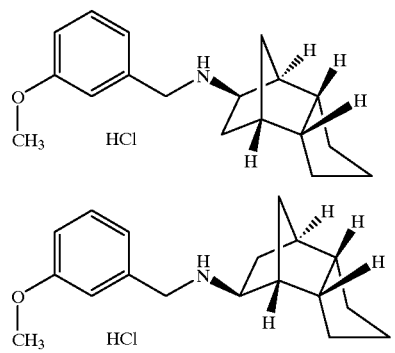

500 mg of rac-(3-methoxybenzyl)(octahydro-4,7-methanoinden-5-yl)amine hydrochloride from Example 5) were separated in a number of runs on a preparative column from Diacel Chemicals (CSP-Chiralpak-AS 250x25, 10 μ). The conditions used were as follows: flow rate: 3 ml/min; temperature: 24° C.; eluent mixture: n-hexane/ethanol/isopropanol/TFA 10/1/1/0.1; and wavelength: 230 nm.

Freeze-drying gave: (+)-enantiomer: 198 mg, purity by HPLC: 98% (−)-enantiomer: 218 mg, purity by HPLC: 99%

To convert the compounds into the hydrochloride, 75 mg of the enantiomer in question were admixed with potassium carbonate solution and ethyl acetate, and the mixture was shaken well. After phase separation, the aqueous phase was extracted two more times with ethyl acetate. The combined organic phases were dried using magnesium sulfate and filtered, and the filtrate was concentrated under reduced pressure. The residue was taken up in ethyl acetate and filtered over 5 g of silica gel, the filtrate was concentrated, and the residue was admixed with 2 N hydrochloric acid and freeze-dried.

Freeze-drying gave:

(+)-enantiomer: 53 mg, optical rotation: +33°, (Na, 589 nm), MS (ES+): 272.2 (M+H)$^+$ (−)-enantiomer: 51 mg, optical rotation: −32°, (Na, 589 nm), MS (ES+): 272.2 (M+H)$^+$ Example 7

(endo/exo)-(3-methoxybenzyl)(octahydro-4,7-methanoinden-5-yl)amine hydrochloride

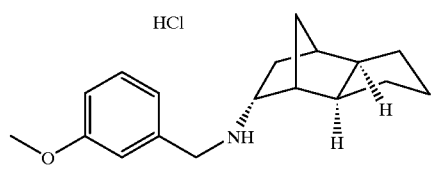

In an autoclave, a mixture of 2.2 g of 3-methoxybenzaldehyde, 40 ml of methanol, 3.3 g of (endo/exo)-octahydro-4,7-methanoinden-5-ylamine (amine 2), and Raney nickel catalyst was hydrogenated at 80° C. and a hydrogen pressure of 60 bar for 6 hours. The residue was dissolved in ethyl acetate, the catalyst was filtered off, the solvent was distilled off under reduced pressure, the mixture was dried over sodium sulfate, and the solvent was once more removed using a rotary evaporator. The residue was dissolved in a little ethyl acetate and admixed with an excess of ethereal hydrochloric acid and, with stirring, a precipitate formed. Colorless crystalline substance (from diisopropyl ether/methanol) of mp. 206–208° C.

Example 8

(endo/endo)-(3-methoxybenzyl)(octahydro-4,7-methanoinden-5-yl)amine hydrochloride

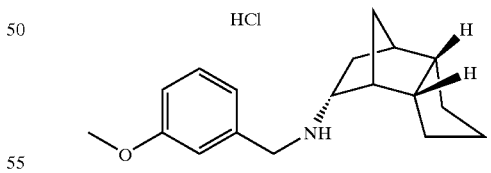

With exclusion of moisture, 190 mg of 3-methoxybenzaldehyde, 211 mg of (endo/endo)-octahydro-4,7-methanoinden-5-ylamine (amine 3), and 423 mg of triethylamine were initially charged in 5 ml of dry CH$_2$Cl$_2$. Using a septum, 0.7 ml of a 1 molar solution of titanium tetrachloride in toluene were added dropwise with stirring. After 18 hours at room temperature, 887 mg of triacetoxy borohydride were added, and the mixture was stirred for a further hour. 3 ml of 5 N sodium hydroxide solution and 10 ml of water were then added, the mixture was extracted three times with 20 ml of ethyl acetate, and the extracts were dried, filtered and concentrated under reduced pressure. The residue was dissolved in 2 N hydrochloric acid and the solution was extracted with ether. The aqueous phase was concentrated and purified by preparative HPLC over RP-18 using acetonitrile/-water. The pure fractions were combined, the acetonitrile was removed using a rotary evaporator, the residue was adjusted to pH 11 using potassium carbonate and extracted with $CH_2Cl_2$, and the combined phases were dried and concentrated. The residue was taken up in 2 N hydrochloric acid and a little acetonitrile and freeze-dried. This gave 10 mg of the hydrochloride as a white solid.

MS (ES+): 272.2 (M+H)+

Example 9

(exo/exo)-(3-methoxybenzyl)(octahydro-4,7-methanoinden-5-yl)amine hydrochloride

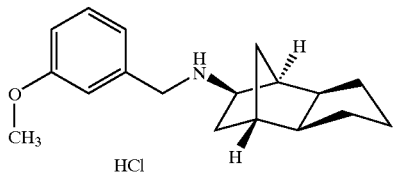

A mixture of 150 mg of 3-methoxybenzaldehyde, 167 mg of (exolexo)-octahydro-4,7-methanoinden-5-ylamine (amine 4), a catalytic amount of p-toluenesulfonic acid, and 15 ml of anhydrous toluene was boiled under reflux for 3 hours, the toluene was distilled off under reduced pressure, and the residue was dissolved in 10 ml of methanol. With ice-cooling, 50 mg of sodium borohydride were added in small portions to this methanolic solution, and the mixture was then allowed to warm to room temperature. A solution of hydrogen chloride in methanol was added, the precipitate was filtered off, and the solvent was distilled off under reduced pressure. The residue was purified by preparative HPLC over RP-18 using acetonitrile/water (0.05% trifluoroacetic acid). The trifluoroacetate, which was obtained after freeze-drying, was converted, using aqueous sodium hydroxide solution/ethyl acetate, into the free amine and then converted into the hydrochloride using 2 N HCl. This gave 125 mg of a white product.

MS (Cl+): 272.2 (M+H)+

Example 10

(exo/endo)-(3-fluorobenzyl)(octahydro-4,7-methanoinden-5-yl)amine hydrochloride

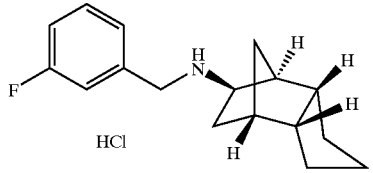

With exclusion of moisture, 124 mg of 3-fluorobenzaldehyde, 151 mg of (exo/endo)-octahydro-4,7-methanoinden-5-ylamine (amine 1), and 303 mg of triethylamine were initially charged in 10 ml of dry $CH_2Cl_2$. Using a septum, 0.5 ml of a 1-molar solution of titanium tetrachloride in toluene were added dropwise with stirring. After 18 hours at room temperature, 3 ml of a 1-molar solution of sodium cyanoborohydride in THF were added, and the mixture was stirred for a further 15 min. 5 ml of 5 N sodium hydroxide solution and 15 ml of water were then added, the mixture was extracted three times with 25 ml of ethyl acetate, and the extracts were dried, filtered, and concentrated under reduced pressure. The residue was filtered over silica gel ($CH_2Cl_2$/methanol 97:3), and once more evaporated to dryness, and the crude product was purified by preparative HPLC over RP-18 using acetonitrile/water. The pure fractions were combined, the acetonitrile was removed using a rotary evaporator, the mixture was adjusted to pH 11 using potassium carbonate and extracted three times with ethyl acetate, and the combined phases were dried and concentrated. The residue was taken up in 2 N hydrochloric acid and a little acetonitrile and freeze-dried. This gave 144 mg of a white solid.

MS (Cl+): 260 (M+H)+

Example 11

(exo/endo)-(3,5-difluorobenzyl)(octahydro-4,7-methanoinden-5-yl)amine hydrochloride

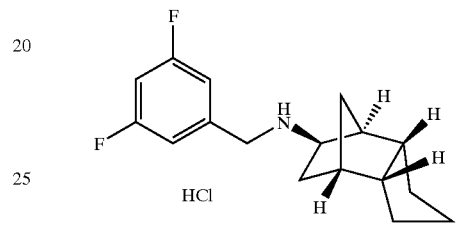

200 mg of 3,5-difluorobenzaldehyde and 151 mg of (exo/endo)-octahydro-4,7-methanoinden-5-ylamine (amine 1) were dissolved in 15 ml of toluene (anhydrous) and admixed with 11 mg of para-toluenesulfonic acid, and the mixture was boiled under reflux for 3 hours. The volatile components were then removed under reduced pressure. The residue was taken up in 10 ml of methanol and, with ice-cooling and stirring, admixed with 64 mg of $NaBH_4$, and the mixture was allowed to stand overnight.

The solution was adjusted to pH 1–2 using methanolic HCl, the precipitated solid was filtered off, and the solution was concentrated. The residue was dissolved in hot ethanol and the solution was filtered and cooled with stirring. The product was precipitated by addition of diethyl ethyl, filtered off with suction, washed with ether, and dried. This gave 212 mg of a white solid.

MS (Cl+): 278.3 (M+H)+

Example 12

(exo/endo)-[1-(3-methoxyphenyl)ethyl](octahydro-4,7-methanoinden-5-yl)amine hydrochloride

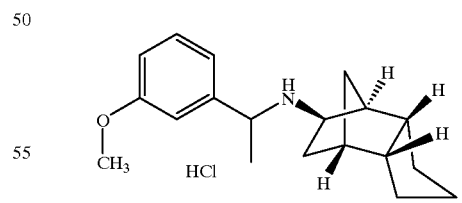

At 5–10° C., a mixture of 0.73 g of titanium tetrachloride and 3 ml of n-pentane was added dropwise over a period of 10 minutes to a solution of 0.75 g of 3-methoxyacetophenone and 2.7 g of (exo/endo)-octahydro-4,7-methanoinden-5-ylamine (amine 1) in 15 ml of n-pentane. The mixture was stirred at 5–10° C. for another hour and then allowed to stand at room temperature overnight. The precipitate was filtered off and the solvent was then distilled off using a rotary evaporator. The residue was then dissolved in 20 ml of methanol and, with cooling at 5–10° C., admixed a little at a time with 0.96 g of sodium borohydride. The mixture was stirred at room temperature for 15–20 hours and the solvent was then distilled off. The residue was admixed with water, acidified with hydrochloric acid, and extracted with ethyl acetate, which resulted in the precipitation of crystals which were filtered off and recrystallized from a little water (mp. 257–259° C.). The aqueous filtrate was made strongly alkaline using 2 N NaOH and extracted with ethyl acetate, the organic solution was dried over sodium sulfate, and the solvent was distilled off. The residue was dissolved in a little ethyl acetate and the solution was then acidified strongly using a solution of hydrogen chloride in diethyl ether, and the crystals were filtered off and recrystallized from a little water (mp. 257–259° C.).

Example 13
(exo/endo)-(3-bromobenzyl)(octahydro-4,7-methanoinden-5-yl)amine hydrochloride

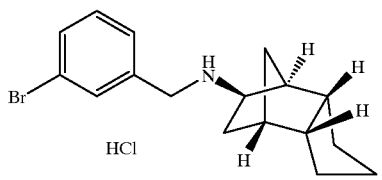

1.9 g of 3-bromobenzaldehyde, 1.5 g of (exo/endo)-octahydro-4,7-methanoinden-5-ylamine (amine 1), and 60 mg of p-toluenesulfonic acid were dissolved in 180 ml of anhydrous toluene, and the mixture was boiled under reflux for 5 hours. The volatile components were removed under reduced pressure and the residue was dissolved in 120 ml of methanol. 530 mg of $NaBH_4$ were added and the mixture was stirred at RT for 2 hours. The mixture was allowed to stand at RT for 18 hours, and the volatile components were then removed under reduced pressure. The residue was taken up in 200 ml of a saturated aqueous $NaHCO_3$ solution, and the mixture was then extracted three times with, in each case, 200 ml of EA. The extracts were dried over $MgSO_4$ and the solvent was removed under reduced pressure. The residue was taken up in 12 ml of a 10% strength aqueous HCl solution and the volatile components were removed under reduced pressure. The residue was stirred with 50 ml of EA, giving 3.0 g of the crystalline hydrochloride, mp 248° C.

$R_f$(EA)=0.44; MS (Cl+): 320 (M+H)$^+$

Example 14
(exo/endo)-3-[(octahydro-4,7-methanoinden-5-ylamino)-methyl]benzoic acid

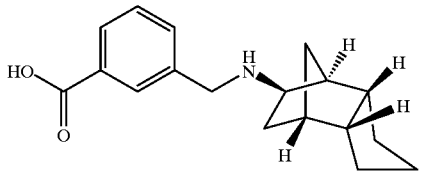

a) butyl 3-[(octahydro-4,7-methanoinden-5-ylamino) methyl]benzoate 1 g of (3-bromobenzyl)(octahydro-4,7-methanoinden-5-yl)amine hydrochloride from Example 13, 115 mg of 1,3-bis(diphenylphosphino)propane, 63 mg of Pd(II) acetate, and 4 ml of tri-n-butylamine were dissolved in 10 ml of 1-butanol and 2 ml of DMF and, at 110° C., stirred under a CO atmosphere (atmospheric pressure) for 8 hours. Another 115 mg of 1,3-bis(diphenylphosphino)propane and 63 mg of Pd(II) acetate were then added, and the mixture was stirred at 110° C. for another 7 hours. After cooling, 100 ml of a saturated aqueous $Na_2CO_3$ solution were added and the mixture was extracted three times with, in each case, 100 ml of EA. The extracts were dried over $MgSO_4$ and the solvent was removed under reduced pressure. Chromatography of the residue over silica gel using DIP/2% triethylamine gave 600 mg of a colorless oil.

$R_f$(DIP/2% triethylamine)=0.42; MS (ES+): 342 (M+H)$^+$ b) 3-[(octahydro-4,7-methanoinden-5-ylamino)methyl] benzoic acid 600 mg of butyl 3-[(octahydro-4,7-methanoinden-5-ylamino)methyl]benzoate were dissolved in 1 ml of n-butanol, and 2.1 ml of a 1 N aqueous NaOH solution were added. The mixture was stirred at RT for 18 hours and then at 60° C. for 4 hours. The volatile components were then removed under reduced pressure and residual n-butanol was then distilled off twice, azeotropically, under reduced pressure, using in each case 5 ml of water. The residue was taken up in 5 ml of a 10% strength aqueous HCl solution, the volatile components were removed under reduced pressure, and the water was distilled off azeotropically twice, under reduced pressure, using in each case 5 ml of toluene. Since the product still contained considerable amounts of starting material, it was once more dissolved, in 6 ml of methanol, and admixed with 1 ml of a 2 N aqueous NaOH solution. The mixture was stirred at RT for 3 hours, and a further 5 ml of a 2 N aqueous NaOH solution were then added and the mixture was boiled under reflux for 4 hours. The volatile components were removed under reduced pressure, the residue was taken up in 20 ml of water, and the mixture was adjusted to pH=7 using dilute aqueous HCl solution. The mixture was stirred at RT for 1 hour and the product was filtered off with suction and dried under reduced pressure. This gave 260 mg of a crystalline solid, mp 258–261° C.

MS (Cl+): 286 (M+H)$^+$

Example 15
(exo/endo)-[3-(2-methoxyethoxy)benzyl](octahydro-4,7-methanoinden-5-yl)amine hydrochloride

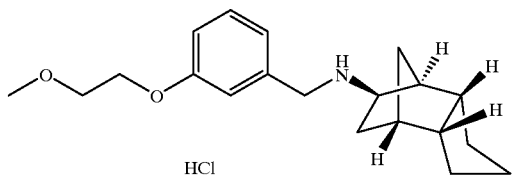

a) 3-(2-methoxyethoxy)benzaldehyde 1.0 g of 3-hydroxybenzaldehyde, 1.1 g of 1-bromo-2-methoxyethane, and 10.7 g of $Cs_2CO_3$ were stirred at 40° C. in 10 ml of DMF (anhydrous) for 4 hours. The mixture was diluted with 100 ml of water and extracted twice with, in each case, 50 ml of EA. The extract was dried over $MgSO_4$ and the solvent was removed under reduced pressure. This gave 1.3 g of a colorless oil.

$R_f$(DIP)=0.24; MS (Cl+): 181 (M+H)$^+$ b) [3-(2-methoxyethoxy)benzyl](octahydro-4,7-methanoinden-5-yl)amine hydrochloride 300 mg of 3-(2-methoxyethoxy)benzaldehyde, 253 mg of (exo/endo)-octahydro-4,7-methanoinden-5-ylamine (amine 1), and 10 mg of p-toluene-sulfonic acid were dissolved in 30 ml of anhydrous toluene, and the mixture was boiled under reflux for 5 hours. The volatile components were removed under reduced pressure and the residue was dissolved in 20 ml of methanol. 90 mg of NaBH$_4$ were added at the mixture was stirred at RT for 2 hours. The mixture was allowed to stand at RT for 18 hours and the volatile components were then removed under reduced pressure. The residue was taken up in 50 ml of a saturated aqueous NaHCO$_3$ solution, and the mixture was extracted three times with, in each case, 50 ml of EA. The extract was dried over MgSO$_4$ and the solvent was removed under reduced pressure. The residue was taken up in 2 ml of a 10% strength aqueous HCl solution and the volatile components were removed under reduced pressure. The residue was stirred with 10 ml of diethyl ether, giving 163 mg of the crystalline hydrochloride, mp 134° C.

R$_f$(EA)=0.30; MS (Cl+): 316 (M+H)$^+$

Example 16

(exo/endo)-(3-iodobenzyl)(octahydro-4,7-methanoinden-5-yl)-amine hydrochloride

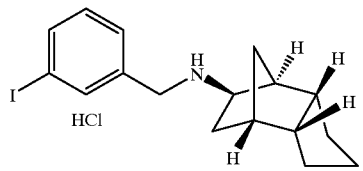

a) 1-bromomethyl-3-iodobenzene 4.4 g of 3-iodotoluene were dissolved in 10 ml of chlorobenzene and, at 132° C., mixed a little at a time with a mixture of 3.6 g of N-bromo-succinimide and 100 mg of dibenzoyl peroxide. The mixture was stirred at 132° C. for another hour and, after cooling, diluted with 100 ml of EA and then washed, first with 100 ml of a saturated aqueous Na$_2$SO$_3$ solution and then with 100 ml of a saturated aqueous Na$_2$CO$_3$ solution. The organic phase was dried over MgSO$_4$ and the solvent was removed under reduced pressure. This gave 5.3 g of a pale yellow oil.

R$_f$(EA/HEP 1:8)=0.44; MS (ES+): 298 (M+H)$^+$ b) (3-iodobenzyl)(octahydro-4,7-methanoinden-5-yl)amine hydrochloride 755 mg of (exo/endo)-octahydro-4,7-methanoinden-5-ylamine (amine 1) and 830 µl of triethylamine were dissolved in 20 ml of anhydrous THF and, at 0° C., admixed slowly with 2.8 g of 1-bromomethyl-3-iodobenzene. The mixture was stirred at 0° C. for 30 minutes and then at RT for 5 days. 100 ml of a saturated aqueous Na$_2$CO$_3$ solution were then added, and the mixture was extracted twice with, in each case, 100 ml of EA. The extract was dried over MgSO$_4$ and the solvent was removed under reduced pressure. The residue was dissolved in 20 ml of methanol and the solution was adjusted to pH<2 using a 10% strength aqueous HCl solution. The volatile components were then removed under reduced pressure and the residue was stirred with 10 ml of EA and dried under reduced pressure. This gave 1.74 g of colorless crystals, mp 220–224° C. (with decomposition)

MS (Cl+): 368 (M+H)$^+$

Example 17

(exo/endo)-3-[(octahydro-4,7-methanoinden-5-ylamino)-methyl]benzonitrile hydrochloride

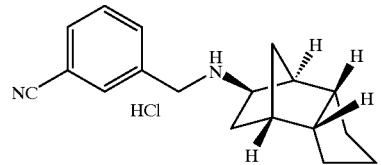

With exclusion of moisture, 750 mg of 3-cyanobenzaldehyde, 865 mg of (exo/endo)-octahydro-4,7-methanoinden-5-ylamine (amine 1), and 1.74 g of triethylamine were initially charged in 30 ml of dry CH$_2$Cl$_2$. Using a septum, 2.86 ml of a 1-molar solution of titanium tetrachloride in toluene were added dropwise with stirring. After 18 hours at room temperature, 17.2 ml of a 1-molar solution of sodium cyanoborohydride in THF were added, and the mixture was stirred for a further 15 min. 20 ml of 5 N sodium hydroxide solution in 60 ml of water were then added, the mixture was then extracted three times with 50 ml of ethyl acetate, and the extract was dried, filtered, and concentrated under reduced pressure. The residue was filtered through silica gel (CH$_2$Cl$_2$/methanol 97:3), and once more evaporated to dryness, and the crude product was purified by preparative HPLC over RP-18 using acetonitrile/water (0.05% trifluoroacetic acid). Freeze-drying gave 1.1 g of the desired product as a white powder in the form of the trifluoroacetate.

250 mg of this powder were, as described in Example 9, converted into the hydrochloride. This gave 175 mg of a white solid.

MS (Cl+): 267.3 (M+H)$^+$

Example 18 methyl (exo/endo)-3-[(octahydro-4,7-methanoinden-5-yl-amino)methyl]benzoate hydrochloride and ethyl (exo/endo)-3-[(octahydro-4,7-methanoinden-5-ylamino)methyl]-benzoate hydrochloride

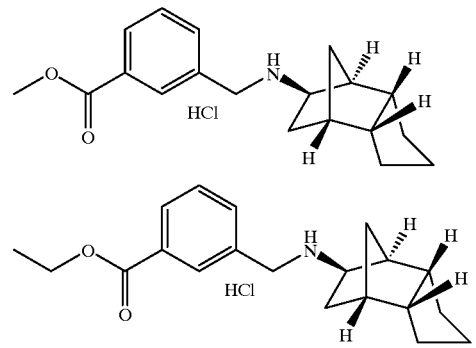

a) ethyl (exo/endo)-3-[(octahydro-4,7-methanoinden-5-ylamino)methyl] benzimidate dihydrochloride 500 mg of 3-[(octahydro-4,7-methanoinden-5-ylamino)methyl]benzonitrile trifluoroacetate from Example 17 were dissolved in 20 ml of dry ethanol (denatured with 5% methanol and 5% isopropanol), and hydrogen chloride gas was passed through the solution, with stirring and ice-cooling, for 3 hours. The mixture was allowed to stand at room temperature overnight, and the next day excess hydrogen chloride gas was flushed out using nitrogen and the residue was concentrated. This gave 587 mg of ethyl benzamidate as a white powder, which was contaminated by small amounts of methyl benzamidate.

The crude product was directly reacted further.

b) methyl (exo/endo)-3-[(octahydro-4,7-methanoinden-5-ylamino)methyl]-benzoate hydrochloride and ethyl (exo/endo)-3-[(octahydro-4,7-methanoinden-5-ylamino)methyl]-benzoate hydrochloride 100 mg of the product from a) were dissolved in 6 ml of a mixture of water and trifluoroacetic acid (5:1), and the mixture was stirred at room temperature for 3 hours. The mixture was allowed to stand overnight, and the solvent was then removed and the residue was purified by preparative HPLC over RP-18 using acetonitrile/water (0.05% trifluoroacetic acid). The resulting trifluoroacetate compounds of the ethyl and methyl ester were taken up in potassium carbonate solution and extracted with ethyl acetate. The extract was dried and the ethyl acetate was removed under reduced pressure, and the residue was then admixed with 2 N hydrochloric acid and freeze-dried.

This gave 28 mg of the ethyl ester and 7 mg of the methyl ester.

Methyl ester: MS (ES+). 300.2 (M+H)+

Ethyl ester: MS (ES+): 314.3 (M+H)+

Example 19

(exo/endo)-{3-[(octahydro-4,7-methanoinden-5-ylamino)-methyl]phenyl}methanol hydrochloride

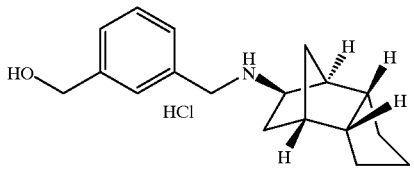

50 mg of a methyl/ethyl ester mixture, prepared as in Example 18 b), and dissolved in 5 ml of THF, were added dropwise, with stirring and exclusion of moisture, to 0.43 ml of a 1-molar solution of lithium aluminum hydride in THF. The mixture was stirred at room temperature and allowed to stand over the weekend, and water was then slowly added dropwise with ice-cooling and the resulting precipitate was filtered off with suction and washed thoroughly with ethyl acetate. The aqueous phase was extracted with ethyl acetate and the combined organic phases were dried with magnesium sulfate. The desiccant was filtered off and the solvent was then removed under reduced pressure and the residue was purified by preparative HPLC over RP-18 using acetonitrile/water (0.05% trifluoroacetic acid). The product was then, as described in Example 10, converted into the hydrochloride.

Freeze-drying gave 7 mg of product.

MS (ES+): 272.2 (M+H)+

Example 20

(exo/endo)-3-[(octahydro-4,7-methanoinden-5-ylamino)-methyl]benzamide trifluoroacetate

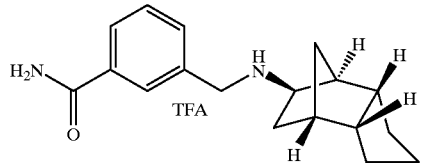

45 mg of ethyl 3-[(octahydro-4,7-methanoinden-5-ylamino)methyl]-benzimidate dihydrochloride from Example 18 a) were heated at 60° C. for 8 hours and then allowed to stand at room temperature for three weeks. The solid was then purified by preparative HPLC over RP-18 using acetonitrile/water (0.05% trifluoroacetic acid). After freeze-drying, 4 mg of the desired product were isolated.

MS (ES+): 285.2 (M+H)+

Example 21

(exo/endo)-(3-aminomethylbenzyl)(octahydro-4,7-methanoinden-5-yl)amine bistrifluoroacetate

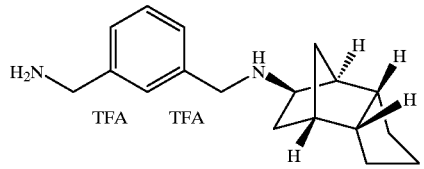

100 mg of 3-[(octahydro-4,7-methanoinden-5-ylamino) methyl]benzonitrile trifluoroacetate from example 17, dissolved in 5 ml of dry THF, were added dropwise to 5 ml of a 1-molar solution of lithium aluminum hydride in THF. The mixture was then heated at 80° C. for 5 hours. With ice-cooling, water was then slowly added dropwise, and the mixture was admixed with aqueous sodium hydroxide solution. The precipitate was filtered off and washed with ether. The aqueous phase was extracted, and the combined organic phases were then dried, and the desiccant was filtered off. The organic phases were concentrated and the residue was purified by preparative HPLC over RP-18 using acetonitrile/water (0.05% trifluoroacetic acid). After freeze-drying, 26 mg of product were isolated.

MS (ES+): 271.2 (M+H)+

Example 22

(exo/endo)-3-[(octahydro-4,7-methanoinden-5-ylamino)-methyl]benzamidine bistrifluoroacetate

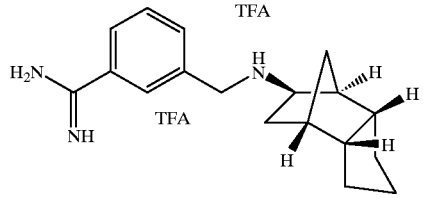

200 mg of ethyl 3-[(octahydro-4,7-methanoinden-5-ylamino)methyl]benzimidate dihydrochloride from Example 18 a) were dissolved in 15 ml of dry ethanol, and about 20 ml of ammonia were slowly condensed into the mixture. The compounds were boiled under reflux in ammonia for 3 hours, and the ammonia was then allowed to evaporate overnight. The residue was concentrated and then purified by preparative HPLC over RP-18 using acetonitrile/water (0.05% trifluoroacetic acid). Freeze-drying gave 89 mg of the desired product.

MS (Cl+): 284.3 (M+H)+

Example 23

(exo/endo)-(3-nitrobenzyl)(octahydro-4,7-methanoinden-5-yl)-amine hydrochloride

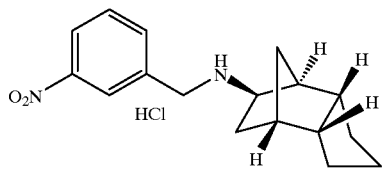

With exclusion of moisture, 750 mg of 3-nitrobenzaldehyde, 751 mg of (exo/endo)-octahydro-4,7-methanoinden-5-ylamine (amine 1), and 1.5 g of triethylamine were initially charged in 30 ml of dry $CH_2Cl_2$. Using a septum, 2.48 ml of a 1-molar solution of titanium tetrachloride in toluene were added dropwise with stirring. After 18 hours at room temperature, 14.89 ml of a 1-molar solution of sodium cyanoborohydride in THF were added, and the mixture was stirred for a further 15 min. 20 ml of 5 N sodium hydroxide solution and 60 ml of water were then added, the mixture was extracted three times with 50 ml of ethyl acetate, and the extracts were dried, filtered, and concentrated under reduced pressure. The residue was filtered through silica gel ($CH_2Cl_2$/methanol 95:5) and again evaporated to dryness, and the crude product was purified by preparative HPLC over RP-18 using acetonitrile/water (0.05% trifluoroacetic acid). Some of the resulting (3-nitrobenzyl)(octahydro-4,7-methanoinden-5-yl)amine trifluoroacetate was partitioned between ethyl acetate and potassium carbonate solution (pH 11). The aqueous phase was extracted three times with ethyl acetate, and the combined organic phases were dried and concentrated. The residue was taken up in 2 N hydrochloric acid and a little acetonitrile and freeze-dried. This gave 300 mg of a white solid.

MS (ES+): 287.2 (M+H)+

Example 24

(exo/endo)-(3-aminobenzyl)(octahydro-4,7-methanoinden-5-yl)amine bistrifluoroacetate

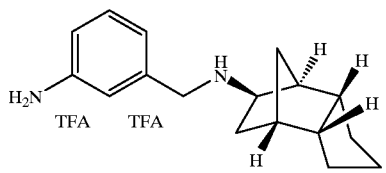

100 mg of (3-nitrobenzyl)(octahydro-4,7-methanoinden-5-yl)amine trifluoroacetate from Example 23 were dissolved in a mixture containing 5 ml of ethanol and 5 ml of glacial acetic acid. 57 mg of zinc powder were then added, and the mixture was stirred at 60° C. for 4 hours. A further 25 g of zinc powder were then added, and the mixture was stirred for another two hours at 60° C. The reaction mixture was concentrated, the residue was taken up in ethyl acetate, and the organic phase was washed three times with potassium carbonate solution, dried, filtered, and concentrated. The residue was purified by preparative HPLC over RP-18 using acetonitrile/water (0.05% trifluoroacetic acid). Freeze-drying gave 23 mg of the desired product.

MS (ES+): 257.2 (M+H)+

Example 25

(exo/endo)-(3-methoxybenzyl)methyl(octahydro-4,7-methanoinden-5-yl)amine hydrochloride

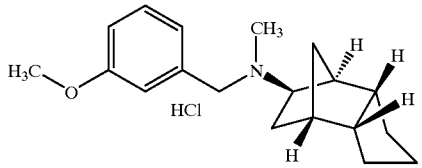

50 mg of (exo/endo)-(3-methoxybenzyl)(octahydro-4,7-methanoinden-5-yl)-amine from Example 5 were initially charged in 5 ml of dry acetone, 20 mg of potassium carbonate were added, the mixture was stirred for 30 min, and 9 µl of methyl iodide were then added dropwise. The reaction mixture was allowed to stand over the weekend and then concentrated, the residue was taken up in water and ethyl acetate, the phases were separated, the aqueous phase was extracted twice with ethyl acetate, and the combined organic phases were dried, filtered, and concentrated. The residue was chromatographed over silica gel using ethyl acetate/heptane. The resulting amine was taken up in 2 N hydrochloric acid and freeze-dried. This gave 14 mg of the desired product.

MS (Cl+): 286.4 (M+H)+

Example 26

(exo/endo)-(3-methoxybenzyl)dimethyl(octahydro-4,7-methanoinden-5-yl)ammonium trifluoroacetate

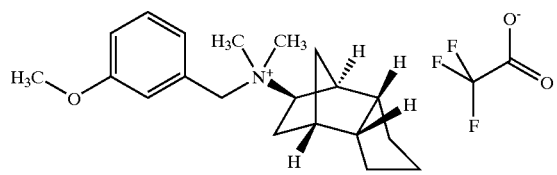

53 mg of (exo/endo)-(3-methoxybenzyl)(octahydro-4,7-methanoinden-5-yl)-amine from Example 5 were initially charged in 5 ml of dry acetone, and 61 µl of methyl iodide were then added dropwise. The mixture was allowed to stand over the weekend, and a further 50 µl of methyl iodide were then added. The mixture was allowed to stand overnight, 3 drops of N-ethyldiisopropylamine were added, and the mixture was then stirred for a further 5 hours. The reaction mixture was then concentrated and purified by preparative HPLC over RP-18 using acetonitrile/water (0.05% trifluoroacetic acid). Freeze-drying gave 53 mg of the desired product.

MS (ES+): 300.3 (M+)

Example 27

(exo/exo)-(3-fluorobenzyl)(octahydro-4,7-methanoinden-5-yl)-amine hydrochloride

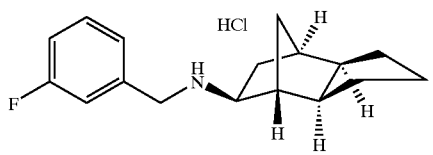

A mixture of 80 mg of 3-fluorobenzaldehyde, 97 mg of (exo/exo)-octahydro-4,7-methanoinden-5-ylamine (amine 4), a catalytic amount of p-toluene-sulfonic acid, and 7.5 ml of anhydrous toluene was boiled under reflux for 3 hours, the toluene was distilled off under reduced pressure, and the residue was dissolved in 5 ml of methanol. With ice-cooling, 29 mg of sodium borohydride were added in small portions to this methanolic solution, and the mixture was allowed to warm to room temperature. 2 N HCl was added, and the precipitate was then filtered off, dissolved in hot ethanol, cooled, and admixed with ether. The resulting precipitate was taken up in 2 N NaOH and dichloromethane, the aqueous phase was separated off, and the organic phase was washed with 2 N NaOH. The organic phase was then dried with MgSO$_4$, filtered, and concentrated. The residue was then converted into the hydrochloride using 2 N HCl. This gave 35 mg of a white product.

MS (Cl+): 260.0 (M+H)$^+$

Example 28

(exo/endo)-(2-trifluoromethylbenzyl)(octahydro-4,7-methanoinden-5-yl)amine hydrochloride

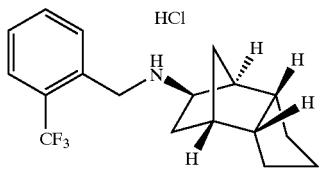

With stirring, 158 mg of 2-(trifluoromethyl)benzyl bromide, dissolved in 2 ml of dichloromethane, were slowly added dropwise to a mixture of 98 mg of (exo/endo)-octahydro-4,7-methanoinden-5-ylamine (amine 1), 103 mg of diisopropylethylamine, and 2 ml of dichloromethane. The mixture was allowed to stand overnight, and the solvent was then removed under reduced pressure and the residue was purified by preparative HPLC over RP-18 using acetonitrile/water (0.05% trifluoroacetic acid). The fractions containing the product were combined, the acetonitrile removed in vaccuo and potassium carbonate solution (pH 11) and ethyl acetate added. The aqueous phase was extracted three times with ethyl acetate, and the combined organic phases were dried and concentrated. The residue was taken up in 2 N hydrochloric acid and a little acetonitrile and freeze-dried. Freeze-drying gave 127 mg of the desired product.

MS (Cl+): 310.2 (M+H)$^+$

Example 29

(exo/endo)-(3-dimethylaminobenzyl)(octahydro-4,7-methanoinden-5-yl)amine hydrochloride

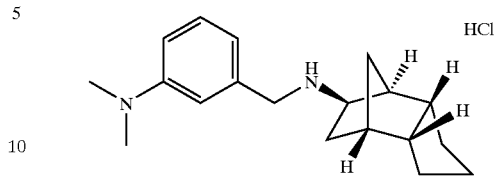

a) (exo/endo)-3-dimethylamino-N-(octahydro-4,7-methanoinden-5-yl)-benzamide 1.78 g (0.011 mol) of N,N-carbonyldiimidazole were added to a solution of 1.65 g (0.01 mol) of 3-N,N-dimethylaminobenzoic acid in 40 ml of anhydrous THF. The mixture was stirred for 3 hours at room temperature under an atmosphere of argon and then admixed with 1.82 g (0.012 mol) of (exo/endo)-octahydro-4,7-methanoinden-5-ylamine (amine 1). The mixture was stirred at room temperature for one hour and allowed to stand overnight, and the solvent was then distilled off. The residue was admixed with water and adjusted to pH 3–4 using 2 N HCl. The mixture was stirred magnetically for about 30 minutes, and the colorless crystalline (exo/endo)-3-dimethylamino-N-(octahydro-4,7-methanoinden-5-yl)benzamide was then filtered off, washed with water, and dried in a stream of air. mp.: 152–156° C.;

MS (Cl+): 299.4 (M+H)$^+$ b) (exo/endo)-(3-dimethylaminobenzyl)(octahydro-4,7-methanoinden-5-yl)-amine hydrochloride A solution of 2 g (0.0067 mol) of (exo/endo)-3-dimethylamino-N-(octahydro-4,7-methanoinden-5-yl) benzamide in 100 ml of anhydrous 1,2-dimethoxyethane was admixed first with 1.38 g (0.0097 mol) of boron trifluoride etherate and then, at 10–15° C. and a little at a time, with 1.13 g (0.03 mol) of sodium borohydride. The mixture was heated at 70° C. for a number of hours and later at 90° C. and allowed to stand overnight. The solvent was then distilled off and the residue was admixed with water and made strongly alkaline using 2 N NaOH. The mixture was extracted 4 times with ethyl acetate, the organic phase was washed with water and dried, and the solvent was evaporated. The residue was subjected to silica gel column chromatography using a mixture of 1 part of ethyl acetate and 3 parts of toluene and then admixed with a solution which contained an excess of hydrogen chloride. The precipitate (exo/endo)-(3-dimethylaminobenzyl)-(octahydro-4,7-methanoinden-5-yl)amine hydrochloride was filtered off and dried. Colorless crystalline solid, mp.: 166–170° C. (with decomposition).

MS (Cl+): 285.2 (M+H)$^+$

Example 30

(exo/endo)-[2-(3-methoxyphenyl)ethyl](octahydro-4,7-methanoinden-5-yl)amine hydrochloride

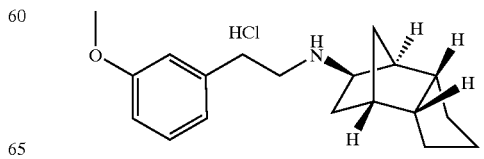

a) (exo/endo)-2-(3-methoxyphenyl)-N-(octahydro-4,7-methanoinden-5-yl)-acetamide (exo/endo)-2-(3-methoxyphenyl)-N-(octahydro-4,7-methanoinden-5-yl)-acetamide was obtained analogously to the procedure given in Example 29 a) from 3-methoxyphenylacetic acid, N,N'-carbonyldiimidazole, and (exo/endo)-octahydro-4,7-methanoinden-5-ylamine (amine 1). Yellow viscous oil.

MS (Cl+): 300.4 (M+H)+ b) (exo/endo)-[2-(3-methoxyphenyl)ethyl](octahydro-4,7-methanoinden-5-yl)amine hydrochloride (exo/endo)-[2-(3-methoxyphenyl)ethyl](octahydro-4,7-methanoinden-5-yl)-amine hydrochloride was obtained analogously to the procedure given in Example 29 b) by reduction of (exo/endo)-2-(3-methoxyphenyl)-N-(octahydro-4,7-methanoinden-5-yl)acetamide. Colorless crystalline solid, mp.: 222–225° C.;

MS (ES+): 286.3 (M+H)+

Example 31
(exo/endo)-[3-(3-methoxyphenyl)propyl](octahydro-4,7-methanoinden-5-yl)amine hydrochloride

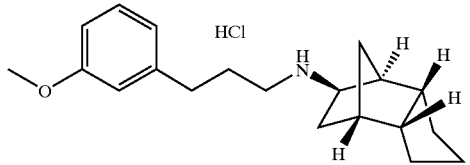

a) (exo/exo)-3-(3-methoxyphenyl)-N-(octahydro-4,7-methanoinden-5-yl)-propionamide (exo/exo)-3-(3-methoxyphenyl)-N-(octahydro-4,7-methanoinden-5-yl)-propionamide was obtained analogously to the procedure given in Example 29 a) from 3-methoxyphenylpropionic acid, N,N'-carbonyldiimidazole, and (exo/endo)-octahydro-4,7-methanoinden-5-ylamine (amine 1). Light-yellow oily product.

MS (Cl+): 314.0 (M+H)+ b) (exo/endo)-[3-(3-methoxyphenyl)propyl](octahydro-4,7-methanoinden-5-yl)amine hydrochloride (exo/endo)-[3-(3-methoxyphenyl)propyl](octahydro-4,7-methanoinden-5-yl)-amine hydrochloride was obtained analogously to the procedure given in Example 29 b) by reduction of (exo/exo)-3-(3-methoxyphenyl)-N-(octahydro-4,7-methanoinden-5-yl)propionamide. Colorless crystalline solid, mp.: 186–188° C.

MS (ES+): 300.3 (M+H)+

Example 32
(exo/endo)-(decahydro-1,4-methanonaphthalen-2-yl)-(3-methoxybenzyl)amine hydrochloride

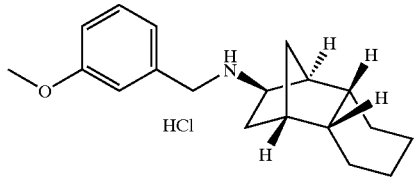

a) bis-(3-chloro-1,2,3,4-tetrahydro-1,4-methanonaphthalen-2-yl)diazene N,N'-dioxide 3.34 g of isoamyl nitrite were added to a solution of 3.56 g of benzonorbornadiene [L. Friedman and F. M. Logullo, J.Org.Chem. 34: 3089–3092, (1969)] in 6 ml of glacial acetic acid and 6 ml of ethanol, and 8.5 ml of a 15% strength solution of hydrogen chloride gas in ethanol were then added dropwise. The resulting suspension was stirred at room temperature for 2½ hours and then mixed with 20 mg of diisopropyl ether. The mixture was stirred for a further 30 minutes and the solid was then filtered off. Clear crystalline solid; mp. 187–188° C.

MS (FAB): 415.1 (M+H)+ b) (exo)-1,2,3,4-tetrahydro-1,4-methanonaphthalen-2-ylamine 3 g of bis-(3-chloro-1,2,3,4-tetrahydro-1,4-methanonaphthalen-2-yl)diazene N,N'-dioxide were suspended in 150 ml of methanol and hydrogenated with Raney nickel catalyst in an autoclave using hydrogen at 100 bar, 100° C., for 20 hours. The catalyst was filtered off, the solvent was evaporated, and the residue was admixed with water, made strongly alkaline using NaOH, and extracted repeatedly with methyl tert-butyl ether. The organic phases were dried, giving the desired amine as a light-yellow liquid.

MS (ES+): 160.0 (M+H)+ c) (exo/endo)-decahydro-1,4-methanonaphthalen-2-ylamine

A solution of 1 g of exo-1,2,3,4-tetrahydro-1,4-methanonaphthalen-2-yl-amine in 10 ml of methanol and 30 ml of 2 N hydrochloric acid was hydrogenated in an autoclave with 0.4 g of RuO2 using hydrogen at 100 bar, 90° C., for 10 hours. The catalyst was separated off, and the mixture was evaporated to half of its original volume. The resulting aqueous solution was made strongly alkaline using 10 N NaOH and extracted repeatedly with methyl tert-butyl ether. The extracts were dried and the solvent evaporated, giving exo-decahydro-1,4-methanonaphthalen-2-yl-amine as a colorless oil which was preferably stored under argon.

MS (Cl+): 166.2 (M+H)+ d) (exo/endo)-(decahydro-1,4-methanonaphthalen-2-yl)-(3-methoxybenzyl)-amine hydrochloride 0.97 g of (exo/endo)-decahydro-1,4-methanonaphthalen-2-ylamine were dissolved in 25 ml of anhydrous toluene and, after addition of 0.8 g of 3-methoxybenzaldehyde and a small catalytic amount of p-toluenesulfonic acid, boiled under reflux for 3 hours. The solvent was evaporated, the residue was dissolved in 50 ml of methanol, 0.26 g of sodium borohydride were added a little at a time with stirring, and the mixture was stirred at room temperature for about 20 hours. The mixture was then acidified using a solution of hydrogen chloride gas in methanol and stirred for 30 minutes, and the precipitated salt was filtered off. The filtrate was concentrated and the residue was recrystallized from a mixture of diisopropyl ether and ethanol. Colorless crystalline substance; mp. 234–236° C.

MS (ES+): 286.3 (M+H)+

The compounds described below were prepared according to the stated example:

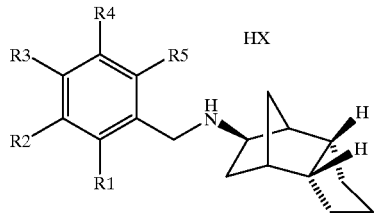

| Example | Analogously to Example | R1 | R2 | R3 | R4 | R5 | HX | MS |
|---|---|---|---|---|---|---|---|---|
| 33 | 5 | —H | —H | —OCH₃ | —H | —H | HCl | Cl+ (M + H)⁺ 272.3 |
| 34 | 5 | —OCH₃ | —H | —H | —H | —H | HCl | Cl+ (M + H)⁺ 272.3 |
| 35 | 5 | —H | —OCH₃ | —H | —H | —OCH₃ | HCl | ES+ (M + H)⁺ 302.2 |
| 36 | 5 | —H | —OCH₂O— | | —H | —H | HCl | ES+ (M + H)⁺ 286.2 |
| 37 | 5 | —H | —OCH₃ | —OCH₃ | —H | —H | — | Cl+ (M + H)+ 302.4 |
| 38 | 5 | —OCH₃ | —H | —OCH₃ | —H | —H | HCl | ES+ (M + H)⁺ 302.3 |
| 39 | 5 | —H | —OCH₃ | —F | —H | —H | HCl | Cl+ (M + H)⁺ 290.3 |
| 40 | 5 | —H | —OH | —H | —H | —H | HCl | Cl+ (M + H)⁺ 258.2 |
| 41 | 10 | —H | —OCF₃ | —H | —H | —H | TFA | ES+ (M + H)⁺ 326.2 |
| 42 | 10 | —H | —OEt | —H | —H | —H | HCl | Cl+ (M + H)⁺ 286.3 |
| 43 | 10 | —H | —OCF₂—CF₂H | —H | —H | —H | TFA | ES+ (M + H)⁺ 358.2 |
| 44 | 10 | —H | —OPrⁱ | —H | —H | —H | HCl | Cl+ (M + H)⁺ 300.3 |
| 45 | 10 | —H | —OEt | —OCH₃ | —H | —H | TFA | ES+ (M + H)⁺ 316.3 |
| 46 | 5 | —H | —CH₃ | —H | —H | —H | HCl | Cl+ (M + H)⁺ 256.3 |
| 47 | 10 | —H | —CF₃ | —H | —H | —H | HCl | Cl+ (M + H)⁺ 310.3 |
| 48 | 5 | —OCH₃ | —CO₂CH₃ | —OCH₃ | —H | —H | HCl | ES+ (M + H)⁺ 360.2 |
| 49 | 11 | —H | —F | —F | —F | —H | HCl | Cl+ (M + H)⁺ 296.3 |
| 50 | 5 | —H | —Cl | —H | —H | —H | HCl | Cl+ (M + H)⁺ 276.2 |
| 51 | 5 | —H | —SO₂NH₂ | —Cl | —H | —H | HCl | Cl+ (M + H)⁺ 355.1 |

-continued
| | | | | | | | | |
|---|---|---|---|---|---|---|---|---|
| 52 | 5 | —H | 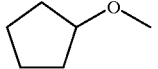 | —H | —H | —H | HCl | CI+ (M + H)+ 326.2 |
| 53 | 5 | —H | 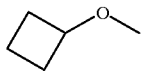 | —H | —H | —H | HCl | CI+ (M + H)+ 312.2 |
| 54 | 5 | —H | 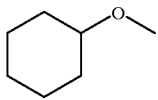 | —H | —H | —H | HCl | CI+ (M + H)+ 340.2 |
| 55 | 28 | —H | —F | —F | —H | —H | HCl | ES+ (M + H)+ 278.2 |
| 56 | 28 | —H | —OCH$_3$ | —H | —OCH$_3$ | —H | HCl | ES+ (M + H)+ 302.3 |
| 57 | 5 | —H | —CH$_2$CH$_3$ | —H | —H | —H | HCl | CI+ (M + H)+ 270.1 |
| 58 | 28 | —F | —H | —H | —H | —H | HCl | CI+ (M + H)+ 260.2 |
| 59 | 28 | —SCF$_3$ | —H | —H | —H | —H | HCl | CI+ (M + H)+ 342.0 |
| 60 | 28 | —H | —H | —OCF$_3$ | —H | —H | HCl | ES+ (M + H)+ 326.2 |
| 61 | 5 | —H | —SCH$_3$ | —H | —H | —H | HCl | ES+ (M + H)+ 288.2 |
| 62 | 28 | —H | —H | —CF$_3$ | —H | —H | HCl | ES+ (M + H)+ 310.2 |
| 63 | 9 | —OH | —OCH$_3$ | —H | —NO$_2$ | —H | TFA | ES+ (M + H)+ 333.2 |
| 64 | 9 | —H | 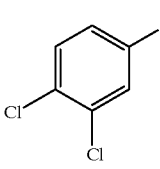 | —H | —H | —H | TFA | ES+ (M + H)+ 402.2 ($^{35}$Cl) |
| Example | | | Analogously to Example | MS |
|---|---|---|---|---|
| 65 | 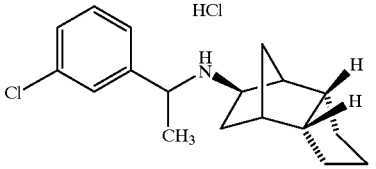 | HCl | 12 | ES+ (M + H)+ 290.1 |
| 66 | 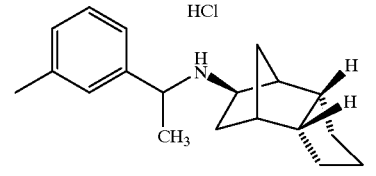 | HCl | 12 | ES+ (M + H)+ 270.2 |

-continued

| | | | | |
|---|---|---|---|---|
| 67 | [structure: 4-methoxy-3-methanesulfonyl-phenyl with CH(CH3)-NH-octahydromethanoindenyl] HCl | | 12 | ES+ (M + H)+ 364.2 |
| 68 | [structure: 4-chloro-3-sulfamoyl-phenyl with CH(CH3)-NH-octahydromethanoindenyl] HCl | | 12 | ES+ (M + H)+ 369.1 |
| 69 | [structure: 4-chloro-3-methanesulfonyl-phenyl with CH(CH3)-NH-octahydromethanoindenyl] HCl | | 12 | ES+ (M + H) 368.2 |

Example 70

(exo/endo)-(3-methanesulfonyl-benzyl)-(octahydro-4,7-methano-inden-5-yl)-amine hydrochloride

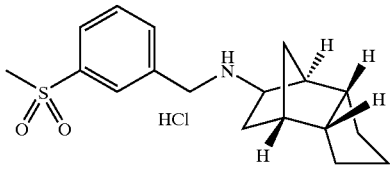

The product of example 61 (65 mg) was dissolved in 3 ml methanol. Then 4 ml of a sodium acetate buffer was added and the mixture was cooled to 0° C. After the slow addition of 617 mg of OXONE® the mixture was stirred for 3 hours at room temperature. Then the precipitate was filtered off and the filtrate concentrated in vaccuo. The residue was treated with sodium bicarbonate and extracted with ethyl acetate. After drying and filtration the organic mixture was concentrated in vaccuo to give 60 mg of crude material that was purified by preparative HPLC over RP-18 using acetonitrile/water (0.05% trifluoroacetic acid). The fractions containing the product were combined, the acetonitrile removed in vaccuo, and potassium carbonate solution (pH 11) and ethyl acetate added. The aqueous phase was extracted three times with ethyl acetate, and the combined organic phases were dried and concentrated. The residue was taken up in 2 N hydrochloric acid and a little acetonitrile and freeze-dried. Freeze-drying gave 8 mg of the desired product.

MS (Cl+): 320.1 (M+H)+

Pharmacological Data:

Description of the Diuresis Experiment:

Method

The salidiuresis experiment was carried out using male Wistar rats having a weight of 155 to 175 g. 16 hours before the start of the experiment, the feed, but not the drinking water, was withdrawn from the animals. The rats were randomized and placed into diuresis cages. The substance from Example 5 was dissolved in drinking water and administered orally at a dosage of 20 mg/kg of body weight in a volume of 10 ml/kg. The control group received, orally, the corresponding volume of drinking water as vehicle. The excretion of urine of each group for the first 5 hours and in the period from 6 to 24 hours was measured. The urine electrolytes sodium and potassium were determined by flame photometry (flame photometer Eppendorf, Hamburg), and chloride was determined potentiometrically (chloride meter Eppendorf). The osmolality of the urine was determined using the freezing-point depression method (osmometer Vogel, Gießen). Urine and electrolyte excretion and osmolality are stated in ml/kg, mmol/kg, and mosmol/kg of body weight, respectively. The ratio of $Na^+/K^+$ is an indication of the quality of effect of a diuretic. The results given in the table are arithmetic means with standard deviation.

Results:

| | | | Urine ml/kg | mmol/kg Na | K | Cl | Osmolality mosmol/kg | Na/K |
|---|---|---|---|---|---|---|---|---|
| Vehicle control | mean | 1–5 hours | 9.73 | 0.26 | 0.48 | 0.38 | 6.48 | 0.61 |

-continued

| | | | Results: | | | | |
| | | | Urine | mmol/kg | | | Osmolality | |
| | | | ml/kg | Na | K | Cl | mosmol/kg | Na/K |
|---|---|---|---|---|---|---|---|---|
| Drinking water | SD | | 3.69 | 0.14 | 0.20 | 0.23 | 1.33 | 0.36 |
| 10 ml/kg of BW p.o. | mean | 6–24 hours | 26.84 | 1.75 | 3.95 | 1.44 | 32.32 | 0.45 |
| n = 5 | SD | | 6.44 | 0.47 | 0.93 | 0.40 | 7.17 | 0.12 |
| | mean | sum | 36.57 | 2.01 | 4.42 | 1.82 | 38.81 | 0.47 |
| | SD | 1–24 hours | 9.08 | 0.37 | 0.97 | 0.26 | 7.00 | 0.11 |
| Example 5 50 mg in 10 ml | mean | 1–5 hours | 12.39 | 0.31 | 0.75 | 0.60 | 7.82 | 0.47 |
| of drinking water/kg of BW p.o. | mean | 6–24 hours | 22.57 | 1.29 | 3.57 | 1.57 | 30.51 | 0.37 |
| n = 5 | SD | | 6.00 | 0.66 | 0.60 | 0.54 | 5.06 | 0.18 |
| | mean | sum | 34.96 | 1.60 | 4.31 | 2.17 | 38.33 | 0.38 |
| | SD | 1–24 hours | 9.14 | 0.64 | 0.61 | 0.41 | 3.47 | 0.16 |

Assessment: at a dosage of 50 mg/kg orally, the substance from Example 5 showed no salidiuretic effect in rats, compared to the control.

Description of the Caco 2 Model

The Caco 2 cell line was obtained from the American Type Culture Collection (ATCC) and kept in Dulbecco's Modified Eagle Medium (high proportion of glucose), supplemented with non-essential amino acids, L-glutamine, penicillin/streptomycin, and 10% strength fetal calf serum, in an incubator under a 10% $CO_2$ atmosphere at 95% relative atmospheric humidity and at 37° C. The cells were grown in cell culture flasks (175 $cm^2$). For the transport studies, the Caco 2 cells were inoculated onto polycarbonate cell culture inserts (COSTAR TRANSWELLS®, pore size: 3 μm, surface: 4.71 $cm^2$) at a cell density of $6.5 \times 10^4$ cells/$cm^2$ and incubated in six-well culture trays, changing the medium after four and eight days and then every other day. 21- to 25-day-old monolayers were used for the experiments.

In each test series, a 21-day-old monolayer was tested for its properties using $^3$H-dextrane as permeability marker. The value of the transfer rate (cumulative) after 120 min had to be in the range of 2%.

The growth medium was removed from the apical and the basolateral side and the monolayers were then rinsed with the transport buffer (Hank's balanced salt solution pH 7.8; contains 2.8 g/l of glucose), and the cells were equilibrated at 37° C. under a 10% $CO_2$ atmosphere for 15 min. The HBSS buffer is then removed.

The test compounds were dissolved in a mixture of HBSS buffer and DMSO and added to the apical buffer, giving a 1% strength (v/v) DMSO solution. The test concentration for the first experiment was 1 mM, that for the second experiment was 100 μM. The experiments were carried out at 37° C. and started by adding 1.5 ml of test solution on the donor side (apical). Transport buffer without compound was added to the recipient side (basolateral, 2.5 ml). At different intervals, samples were taken from the basolateral side (1 ml) and replaced by fresh buffer solution of a temperature of 37° C. Apical samples were taken at the start and at the end (120 min), so that the recovery rate of the compounds could be determined using these concentrations and the cumulative basolateral concentration. The compounds were analyzed by HPLC.

The apparent permeability coefficient ($P_{app}$) is calculated using the following equation:

$$P_{app} = \frac{d_c \cdot V}{d_t \cdot A \cdot c_o}$$

in which $d_c/d_t$ denotes the flow through the monolayer (μg of compound/(ml×s)), V denotes the liquid volume in the collection chamber (ml), A denotes the surface area of the monolayer ($cm^2$) and $c_0$ denotes the initial concentration (μg of compound/ml) in the donor chamber. The flow through the monolayer was calculated from the cumulative basolateral concentration at the corresponding point of time using the initially linear data curve (linear up to 60 min). All determinations were carried out in three replications, so that the calculated $P_{app}$ value is the mean of three measurements. $P_{app}$ values of selected compounds were correlated with absorptions known from the literature, giving a sigmoidal calibration curve. According to studies by Artursson (Artursson P., Karlsson J.; Biochem. Biophys. Res. Comm. 1991;175/3: 880–885), this curve can be used to assess the fraction of a compound which is absorbed.

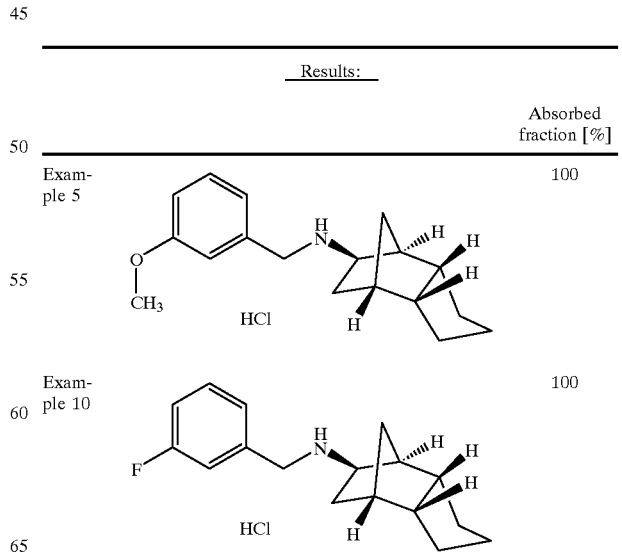

| | | Results: | |
| | | | Absorbed fraction [%] |
|---|---|---|---|
| Example 5 | | | 100 |
| Example 10 | | | 100 |

-continued

Results:

| | | Absorbed fraction [%] |
|---|---|---|
| S 3226 | 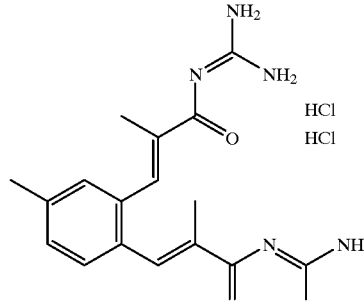 | <5 |
| S 2120 | 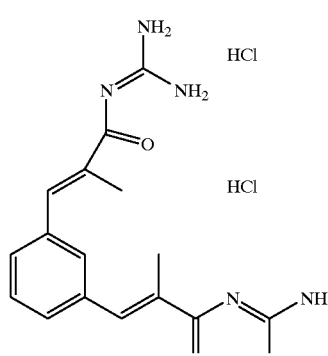 | <1 |

The ability of the compounds of the formula I or I a to cross membranes is considerably superior to that of the NHE3-active compounds of the acylguanidine type known from the literature (J.-R. Schwark et al. Eur. J. Physiol (1998) 436:797).

Description of the NHE Activity Measurements:

Most molecular biology techniques follow protocols from the works "Current Protocols in Molecular Biology (eds. Ausubel, F. M., Brent, R., Kingston, R. E., Moore, D. D., Seidman, J. G., Smith, J. A. and Struhl, K.; John Wiley & Sons)" or: "Molecular Cloning: A Laboratory Manual (Sambrock, J., Fritsch, E. F. and Maniatis, T.; Cold Spring Harbor Laboratory Press (1989))". In our studies, stable transfected cell lines were produced which in each case express one of the following NHE subtypes: NHE1 of man (Sardet et al. Cell 56, 271–280 (1989)), NHE2 of the rabbit (Tse et al. J. Biol. Chem. 268, 11917–11924 (1993)), NHE3 from humans (Brant et al. Am. J. Physiol. 269 (Cell Physiol. 38), C198–C206 (1995)) or NHE3 of the rat (Orlowski et al.; J. Biol. Chem. 267, 9331–9339 (1992)).

After adding suitable linker sequences, the cDNA clones of the respective NHE subtypes obtained by Prof. Pouyssegur were cloned into the expression plasmid pMAMneo (obtainable, for example, via CLONTECH, Heidelberg) such that the NheI restriction endonuclease recognition sequence of the plasmid is approximately 20–100 base pairs before the start codon of the respective NHE subtype and the entire coding sequence is present in the construct. In the human NHE3 obtained from human kidney mRNA via RT-PCR, the RT-PCR primer were selected such that the resulting cDNA band had terminal restriction sites which matched pMAMneo.

Using the so-called "calcium phosphate method" (described in Chapter 9.1 of "Current Protocols in Molecular Biology"), the NHE-deficient cell line LAP1 (Franchi et al.; Proc. Natl. Acad. Sci. USA 83, 9388–9392 (1986)) was transfected with the plasmids which contain the respective coding sequences of the NHE subtypes. After selection of transfected cells by means of growth in G418-containing medium (only cells which as a result of transfection contain a neogene can survive under these conditions), a selection was made for functional NHE expression. To do this, the "Acid Load" technique described by Sardet was used (Sardet et al.; Cell 56, 271–280 (1989)). Cells which express a functioning NHE subtype can also compensate in the absence of $CO_2$ and $HCO_3^-$ for the acidification carried out during this test, but untransfected LAP1 cells cannot. After repetition of the "Acid Load" selection several times, the surviving cells were inoculated into microtiter plates such that statistically there should have been one cell per well. Under the microscope, a check was made after approximately 10 days as to how many colonies were growing per well. Cell populations of individual colonies were then investigated with respect to their viability after "Acid Load" using the XTT proliferation kit (Boehringer Mannheim). The best cell lines were used for the further tests, and to avoid a loss of the transfected sequence were cultured under continuous selection pressure in G418-containing medium.

To determine $IC_{50}$-values for the inhibition of the individual NHE subtypes by specific substances, a test developed by S. Faber (Faber et al.; Cell. Physiol. Biochem. 6, 39–49 (1996)), which is based on the "Acid Load" technique, was slightly modified.

In this test, the recovery of the intracellular pH ($pH_i$) after an acidification was determined, which commences with functioning NHE even under bicarbonate-free conditions. To do this, the $pH_i$ was determined using the pH-sensitive fluorescent dye BCECF (Calbiochem, the precursor BCECF-AM is employed). The cells were first loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the $pH_i$ by means of calibration curves. Differing from the protocol described, the cells were incubated in $NH_4Cl$ buffer (pH 7.4) even during the BCECF loading ($NH_4Cl$ buffer: 115 mM NaCl, 20 mM $NH_4Cl$, 5 mM KCl, 1 mM $CaCl_2$, 1 mM $MgSO_4$, 20 mM HEPES, 5 mM glucose, 1 mg/ml BSA; a pH of 7.4 is established using 1 M NaOH). The intracellular acidification was induced by addition of 975 μl of an $NH_4Cl$-free buffer to 25 μl aliquots of the cells incubated in $NH_4Cl$ buffer. The subsequent time of the pH recovery was recorded as 2 minutes in the case of NHE1, as 5 minutes in the case of NHE2 and as 3 minutes in the case of NHE3. To calculate the inhibitory potency of the substances tested, the cells were first investigated in buffers in which a complete pH recovery or no pH recovery at all took place. For the complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM HEPES, 5 mM glucose; a pH of 7.0 is established using 1 M NaOH). For the determination of the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2HPO_4$, 5 mM HEPES, 5 mM glucose; a pH of 7.0 is established using 1 M NaOH). The substances to be tested were prepared in the $Na^+$-containing buffer.

The recovery of the intracellular pH at each tested concentration of a substance was expressed in percent of the maximum recovery. From the percentage values of the pH recovery, the $IC_{50}$ value of the particular substance for the individual NHE subtypes was calculated by means of the program SigmaPlot

| Example | NHE3 activity Rat NHE3 $IC_{50}$ [μM] |
|---|---|
| 5 | 0.81 |
| (+)-6 | 0.5 |
| (−)-6 | 1 |
| 10 | 0.9 |
| 9 | 5 |
| 8 | 70 |
| 7 | 31 |

What is claimed is:

1. A substituted norbornylamino compound having exo-configured nitrogen and an endo-fused five-, six- or seven-membered ring of the formula I or a pharmaceutically acceptable salt or trifluoroacetate salt thereof, or having exo-configured nitrogen and an exo-fused five-, six- or seven-membered ring of the formula I a or a pharmaceutically acceptable salt or trifluroacetate salt thereof

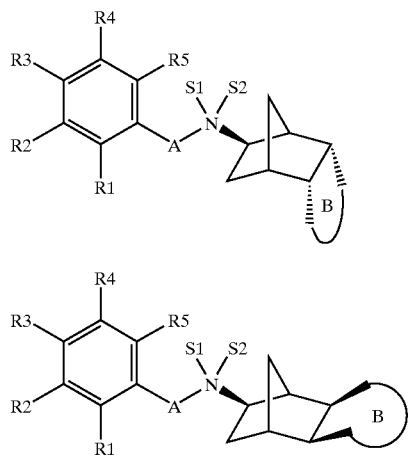

in which:

A is $(C_1-C_4)$-alkylene;

S1 is a free electron pair or $(C_1-C_4)$-alkyl;

S2 is $(C_1-C_4)$-alkyl or H;

where, if S1 and S2 are alkyl, a group $-N^+(S1S2)-X^-$ is obtained, wherein $X^-$ corresponds to a pharmacologically acceptable anion or trifluoroacetate;

B is a saturated or unsaturated five-, six- or seven-membered carbon ring which may be mono- or, independently of one another, polysubstituted by oxo, hydroxyl, $(C_1-C_4)$-alkoxy and $(C_1-C_4)$-alkyl; and R1, R2, R3, R4 and R5 are, independently of one another, H, OH, F, Cl, Br, I, CN, $NO_2$, amidino, $-CO_2R(11)$, $-CONR(11)R(12)$, $-SO_rR(11)$, $-SO_sNR(11)-R(12)$, $(C_1-C_4)$-alkyl, $(C_1-C_4)$-alkoxy, $(C_1-C_4)$-alkoxy-$(C_1-C_4)$-alkyl, $(C_1-C_4)$-alkoxy-$(C_1-C_4)$-alkyloxy, hydroxy-$(C_1-C_4)$-alkyl, $(C_3-C_7)$-cycloalkoxy or phenyloxy, where phenyl is unsubstituted or substituted by up to three substituents, which are independent of one another and are F, Cl, Br, or methoxy; amino, $(C_1-C_4)$-alkylamino, di-$(C_1-C_4)$-alkylamino, amino-$(C_1-C_4)$-alkyl, di-$(C_1-C_4)$-alkylamino-$(C_1-C_4)$-alkyl, $(C_1-C_4)$-alkylamino-$(C_1-C_4)$-alkyl, where some or all of the hydrogen atoms in the alkyl radicals may be substituted by fluorine;

R11 and R12 are, independently of one another, H or $(C_1-C_4)$-alkyl, where some or all of the hydrogen atoms in the alkyl radicals may be substituted by fluorine;

r is 0, 1 or 2;

s is 1 or 2; or at least one of R1 and R2, R2 and R3, R3 and R4 or R4 and R5 together form one or more groups $-O-(CH_2)_n-O-$;

n is 1 or 2; and the radical or radicals R1, R2, R3, R4 or R5 which do not form said group or groups $-O-(CH_2)_n-O-$ is or are, independently of one another, H, OH, F, Cl, Br, I, CN, $NO_2$, amidino, $-CO_2R(11)$, $-CONR(11)R(12)$, $-SO_rR(11)$, $-SO_sNR(11)-R(12)$, $(C_1-C_4)$-alkyl, $(C_1-C_4)$-alkoxy, $(C_1-C_4)$-alkoxy-$(C_1-C_4)$-alkyl, $(C_3-C_7)$-cycloalkoxy, hydroxy-$(C_1-C_4)$-alkyl, amino, $(C_1-C_4)$-alkyl-amino, di-$(C_1-C_4)$-alkylamino, amino-$(C_1-C_4)$-alkyl, di-$(C_1-C_4)$-alkylamino-$(C_1-C_4)$-alkyl, $(C_1-C_4)$-alkylamino-$(C_1-C_4)$-alkyl, where some or all of the hydrogen atoms in the alkyl radicals may be substituted by fluorine;

R11 and R12 are, independently of one another, H or $(C_1-C_4)$-alkyl, where some or all of the hydrogen atoms in the alkyl radicals may be substituted by fluorine;

r is 0, 1 or 2;

s is 1 or 2;

except for benzyl(octahydro-4,7-methanoinden-5-yl)amine.

2. A compound of claim 1, having exo-configured nitrogen and an endo-fused five- or six-membered ring of the formula I, or having exo-configured nitrogen and an exo-fused five- or six-membered ring of the formula I a, in which:

A is $(C_1-C_2)$-alkylene;

S1 is a free electron pair or methyl;

S2 is H;

B is a saturated or unsaturated five- or six-membered carbon ring;

R1, R2, R3, R4 and R5 are, independently of one another, H, amino, hydroxymethyl, OH, methoxy, F, Cl, Br or iodine; or R2 and R3 together are $-O-CH_2-O-$; and the remaining radicals R1, R4 and R5 are, independently of one another, H, OH, F, Cl, Br, I, CN, $NO_2$, $(C_1-C_2)$-alkoxy, amino, $(C_1-C_2)$-alkylamino or di-$(C_1-C_2)$-alkylamino, where some or all of the hydrogen atoms in the alkyl radicals may be substituted by fluorine; or a pharmaceutically acceptable salt or trifluoroacetate salt thereof.

3. A compound of claim 1, having exo-configured nitrogen and an endo-fused five- or six-membered ring of the formula I, or having exo-configured nitrogen and an exo-fused five- or six-membered ring of the formula I a, in which:

A is $(C_1-C_2)$-alkylene;

S1 is a free electron pair;

S2 is H;

B is a saturated or unsaturated five- or six-membered carbon ring;

R1, R3 and R5 are hydrogen;

and R2 and R4 are, independently of one another, H, methoxy, F or Cl; or

R2 and R3 together are —O—CH$_2$—O—; and

R1, R4 and R5 are hydrogen;

or a pharmaceutically acceptable salt thereof.

4. A compound of claim 1, having exo-configured nitrogen and an endo-fused five- or six-membered ring of the formula I, or having exo-configured nitrogen and an exo-fused five-membered ring of the formula I a, wherein the compound is:

exo/endo-(3-chlorobenzyl)(octahydro-4,7-methanoinden-5-yl)amine, exo/endo-(3-fluorobenzyl)(octahydro-4,7-methanoinden-5-yl)amine, exo/endo-benzo[1,3]dioxol-5-ylmethyl(octahydro-4,7-methanoinden-5-yl)amine, exo/endo-(rac)-(3-methoxybenzyl)(octahydro-4,7-methanoinden-5-yl)amine, exo/endo-(+)-(3-methoxybenzyl)(octahydro-4,7-methanoinden-5-yl)amine, exo/endo-(−)-(3-methoxybenzyl)(octahydro-4,7-methanoinden-5-yl)amine, exo/endo-[1-(3-methoxyphenyl)ethyl](octahydro-4,7-methanoinden-5-yl)amine, exo/endo-(3-fluorobenzyl)(3a,4,5,6,7,7a-hexahydro-1H-4,7-methanoinden-5-yl)amine, exo/endo-(3-fluorobenzyl)(3a,4,5,6,7,7a-hexahydro-3H-4,7-methanoinden-5-yl)amine, exo/endo-(3a,4,5,6,7,7a-hexahydro-1H-4,7-methanoinden-5-yl)(3-methoxybenzyl)amine, exo/endo-(3a,4,5,6,7,7a-hexahydro-3H-4,7-methanoinden-5-yl)(3-methoxybenzyl)amine, exo/endo-(decahydro-1,4-methanonaphthalen-2-yl)(3-methoxybenzyl)amine, exo/endo-(3,5-difluorobenzyl)(octahydro-4,7-methanoinden-5-yl)amine, exo/exo-(3-fluorobenzyl)(octahydro-4,7-methanoinden-5-yl)amine, or exo/exo-(3-methoxybenzyl)(octahydro-4,7-methanoinden-5-yl)amine, or a pharmaceutically acceptable salt or trifluoroacetate salt thereof.

5. A compound of claim 1, having exo-configured nitrogen and an endo-fused 5- or 6-membered ring, wherein the compound is:

exo/endo-(3-chlorobenzyl)(octahydro-4,7-methanoinden-5-yl)amine, exo/endo-(3-fluorobenzyl)(octahydro-4,7-methanoinden-5-yl)amine, exo/endo-(3-fluorobenzyl)(3a,4,5,6,7,7a-hexahydro-1H-4,7-methanoinden-5-yl)amine, exo/endo-(3-fluorobenzyl)(3a,4,5,6,7,7a-hexahydro-3H-4,7-methanoinden-5-yl)amine, exo/endo-benzo[1,3]dioxol-5-ylmethyl(octahydro-4,7-methanoinden-5-yl)amine, exo/endo-(rac)-(3-methoxybenzyl)(octahydro-4,7-methanoinden-5-yl)amine, exo/endo-(+)-(3-methoxybenzyl)(octahydro-4,7-methanoinden-5-yl)amine, exo/endo-(decahydro-1,4-methanonaphthalen-2-yl)(3-methoxybenzyl)-amine, exo/endo-(−)-(3-methoxybenzyl)(octahydro-4,7-methanoinden-5-yl)amine, or exo/endo-(3,5-difluorobenzyl)(octahydro-4,7-methanoinden-5-yl)amine, or a pharmaceutically acceptable salt or trifluoroacetate salt thereof.

6. A process for preparing a compound of claim 1, comprising (A) reacting a compound of the formula II or II a

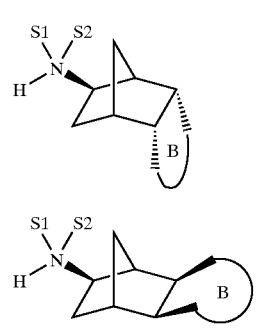

with a compound of the formula III

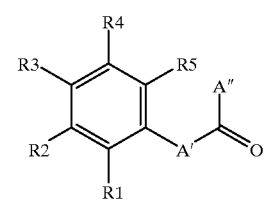

in which S1, S2, B, R1, R2, R3, R4 and R5 are as defined in claim 1, while independently of one another A' is a bond or (C$_1$–C$_3$)-alkylene and A" is H or (C$_1$–C$_3$)-alkyl and A' and A" together with the carbon atom of the carbonyl group represent the same number of carbon atoms as A, in the presence of suitable reducing agents and optionally also Lewis acids directly to give a compound of the formula I or I a, and (B) optionally converting the compound of formula I or I a into a pharmaceutically acceptable salt or trifluoroacetate salt.

7. A process for preparing a compound claim 1, comprising (A) reacting a compound of the formula II or II a

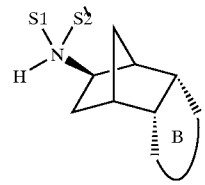

-continued

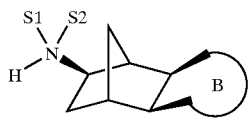
IIa with a compound of the formula III

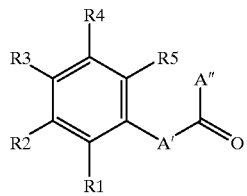
III in which S1, S2, B, R1, R2, R3, R4 and R5 are as defined in claim 1, while independently of one another A' is a bond or (C$_1$–C$_3$)-alkylene and A" is H or (C$_1$–C$_3$)-alkyl and A' and A" together with the carbon atom of the carbonyl group represent the same number of carbon atoms as A, (B) isolating the intermediate of the formula IV or IV a

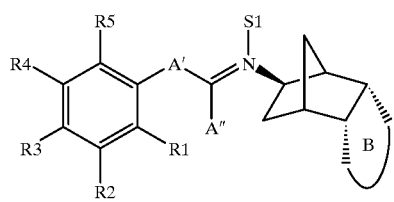
IV

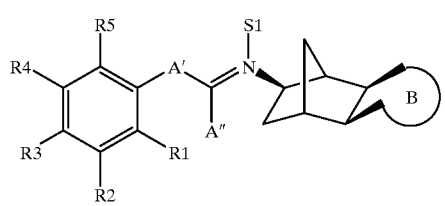
IVa formed from the reaction of the compounds of the formulae II or II a and III, in which, if S1 is (C$_1$–C$_4$)-alkyl, an onium nitrogen is formed which is associated with a counterion, (C) converting the intermediate with suitable reducing agents into a compound of the formula I or Ia, and (D) optionally converting the compound of the formula I or I a into a pharmaceutically acceptable salt or trifluoroacetate salt.

8. A process as claimed in claim 7, wherein the counterion is chloride or tosylate.

9. A process for preparing a compound of claim 1, comprising (A) reacting a compound of the formula II or II a

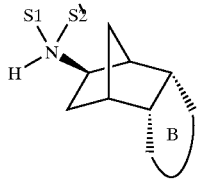
II

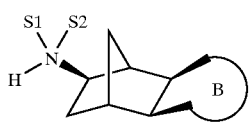
IIa with an alkylating agent of the formula V

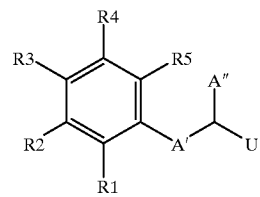
V in which U is a nucleophilically substitutable group, and in which S1, S2, B, R1, R2, R3, R4 and R5 are as defined in claim 1, while independently of one another A' is a bond or (C$_1$–C$_3$)-alkylene and A" is H or (C$_1$–C$_3$)-alkyl and A' and A" together with the carbon atom to which U is attached represent the same number of carbon atoms as A, to give a compound of the formula I or I a, and (B) optionally converting the compound of the formula I or I a into a pharmaceutically acceptable salt or trifluoroacetate salt.

10. A process as claimed in claim 9, wherein U is chlorine, bromine, iodine, mesylate, tosylate, or triflate.

11. A process as claimed in claim 9, wherein the reaction step occurs in the presence of one or more non-nucleophilic bases.

12. A process as claimed in claim 9, wherein the reaction step occurs in the presence of diisopropylethylamine.

13. A process for preparing a compound of claim 1, comprising (A) reducing a carboxamide of the formula VI or VI a

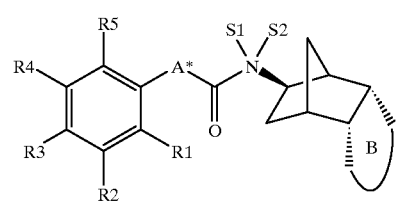
VI

-continued

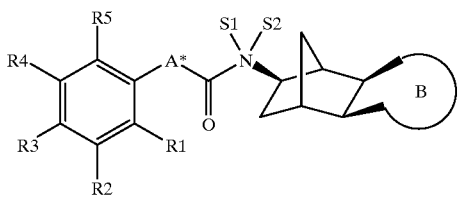

VIa in which A* is a bond or $(C_1-C_3)$-alkylene and the other radicals are as defined in claim 1 to give a corresponding amine of the formula I or I a, and (B) optionally converting the amine into a pharmaceutically acceptable salt or trifluoroacetate salt.

14. A process for converting a secondary amine of the formula I or I a as claimed in claim 1, into a tertiary amine or quaternary ammonium salt, or a pharmaceutically acceptable salt or trifluoroacetate salt thereof, comprising (A) mono- or dialkylating a compound of the formula I or Ia in which S1 is a free electron pair and S2 is hydrogen, with alkylating agents of the formula VII

S*—U   VII in which S* is $(C_1-C_4)$-alkyl and U is a nucleophilically substitutable group, thus obtaining a tertiary amine or a quaternary ammonium salt, and (B) optionally converting the tertiary amine or quaternary ammonium salt into a pharmaceutically acceptable salt or trifluoroacetate salt.

15. A process as claimed in claim 14, wherein U is chlorine, bromine, iodine, mesylate, tosylate, or triflate.

16. A process for preparing a compound claim 1, comprising (A) reacting a dicyclopentadienylplatinum complex of the formula VIII

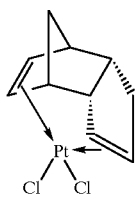

VIII with amines of the type of the formula IX

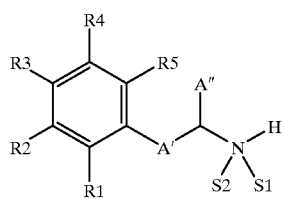

IX in which S1, S2, R1, R2, R3, R4 and R5 are as defined in Claim 1, while independently of one another A' is a bond or $(C_1-C_3)$-alkyl and A" is H or $(C_1-C_3)$-alkyl and A' and A" together with the carbon atom to which the nitrogen atom is attached represent the same number of carbon atoms as A, to form an intermediate, (B) reducing the intermediate formed to give a compound of the formula I, and (C) optionally converting the compound into a pharmaceutically acceptable salt or trifluoroacetate salt.

17. A method of treating snoring, comprising administering an effective amount of a compound of formula I or I a as claimed in claim 1 or a pharmaceutically acceptable salt thereof.

18. A method of treating one or more acute or chronic renal disorders, comprising administering an effective amount of a compound of formula I or I a as claimed in claim 1 or a pharmaceutically acceptable salt thereof.

19. A method as claimed in claim 18, wherein the disorder is acute kidney failure, chronic kidney failure, or both.

20. A method of treating impaired intestinal function, comprising administering an effective amount of a compound of formula I or I a as claimed in claim 1 or a pharmaceutically acceptable salt thereof.

21. A method of treating impaired gallbladder function, comprising administering an effective amount of a compound of formula I or I a as claimed in claim 1 or a pharmaceutically acceptable salt thereof.

22. A method of treating ischemic states of the peripheral nervous system, comprising administering an effective amount of a compound of formula I or I a as claimed in claim 1 or a pharmaceutically acceptable salt thereof.

23. A method of treating ischemic states of the central nervous system, comprising administering an effective amount of a compound of formula I or I a as claimed in claim 1 or a pharmaceutically acceptable salt thereof.

24. A method of treating stroke, comprising administering an effective amount of a compound of formula I or I a as claimed in claim 1 or a pharmaceutically acceptable salt thereof.

25. A method of treating ischemic states of peripheral organs and limbs, comprising administering an effective amount of a compound of formula I or I a as claimed in claim 1 or a pharmaceutically acceptable salt thereof.

26. A method of treating shock, comprising administering an effective amount of a compound of formula I or I a as claimed in claim 1 or a pharmaceutically acceptable salt thereof.

27. A method of treating impaired lipid metabolism, comprising administering an effective amount of a compound of formula I or I a as claimed in claim 1 or a pharmaceutically acceptable salt thereof.

28. A method of treating infestation by ectoparasites, comprising administering an effective amount of a compound of formula I or I a as claimed in claim 1 or a pharmaceutically acceptable salt thereof.

29. A composition comprising a compound of claim 1 and a pharmaceutically acceptable carrier.

30. A composition comprising a compound of claim 4 and a pharmaceutically acceptable carrier.

31. A composition comprising a compound of claim 5 and a pharmaceutically acceptable carrier.

32. A method of treating or preventing hypertension, comprising administering an effective amount of a compound of formula I or I a as claimed in claim 1 or a pharmaceutically acceptable salt thereof.

33. A method of treating a disease caused by elevated cholesterol levels, comprising administering an effective amount of a compound of formula I or I a as claimed in claim 1 or a pharmaceutically acceptable salt thereof.

34. A method of treating a disease caused by endothelial dysfunction, comprising administering an effective amount of a compound of formula I or I a as claimed in claim 1 or a pharmaceutically acceptable salt thereof.

35. A method of inhibiting sodium/proton exchanger, subtype 3 (NHE3), in a patient using a compound of formula I or I a as claimed in claim 1 or a pharmaceutically acceptable salt thereof, comprising giving the patient, for one or more days, up to four doses per day of the compound, wherein the doses are up to 200 mg/kg of body weight.

36. A method of inhibiting sodium/proton exchanger, subtype 3 (NHE3), in a patient using a compound of formula I or I a as claimed in claim 1 or a pharmaceutically acceptable salt thereof, comprising giving the patient, for one or more days, a daily dose of the compound of between 0.001 mg/kg and 100 mg/kg of body weight.

37. A method as claimed in claim 36, wherein the daily dose is between 1 and 10 mg/kg of body weight.

* * * * *

UNITED STATES PATENT AND TRADEMARK OFFICE
CERTIFICATE OF CORRECTION

PATENT NO. : 6,825,231 B2  
APPLICATION NO. : 09/734008  
DATED : November 30, 2004  
INVENTOR(S) : Uwe Heinelt et al.

It is certified that error appears in the above-identified patent and that said Letters Patent is hereby corrected as shown below:

Column 44, line 16, "R4 or R4" should read --R4, and R4--;

Column 44, line 20, "R4 or R5" should read --R4 and R5--;

Column 46, line 4, "methoxybenzyl)-amine," should read --methoxybenzyl)amine,--;

Column 49, line 35, "compound claim" should read --compound of claim--.

Signed and Sealed this

Sixth Day of March, 2007

JON W. DUDAS  
*Director of the United States Patent and Trademark Office*